US006638264B1

(12) United States Patent
Tryggvason et al.

(10) Patent No.: US 6,638,264 B1
(45) Date of Patent: Oct. 28, 2003

(54) PERFUSION APPARATUS AND METHODS FOR PHARMACEUTICAL DELIVERY

(75) Inventors: Karl Tryggvason, Djureholm (SE); Olavi Lukkarinen, Oulu (FI); Pirkko Heikkilä, Turku (FI); Teija Parpala, Oulu (FI)

(73) Assignee: Biostratum Incorporation, Durham, NC (US)

( * ) Notice: Subject to any disclaimer, the term of this patent is extended or adjusted under 35 U.S.C. 154(b) by 461 days.

(21) Appl. No.: 09/609,150

(22) Filed: Jun. 30, 2000

Related U.S. Application Data

(63) Continuation-in-part of application No. 09/167,894, filed on Oct. 7, 1998, which is a continuation of application No. 08/761,793, filed on Dec. 6, 1996, now Pat. No. 5,871,464, which is a continuation of application No. 08/442,189, filed on May 16, 1995, now abandoned, and a continuation-in-part of application No. 08/952,501, filed as application No. PCT/IB96/00463 on May 16, 1996.
(60) Provisional application No. 60/142,251, filed on Jul. 2, 1999.

(51) Int. Cl.[7] ............................................. A61M 31/00
(52) U.S. Cl. ........................................ 604/500; 604/131
(58) Field of Search ................................. 604/500, 502, 604/503, 522, 43, 45, 131, 151; 424/93.2; 435/320.1, 325, 455

(56) References Cited

U.S. PATENT DOCUMENTS

| 3,639,084 | A | | 2/1972 | Goldhaber |
| 5,061,241 | A | | 10/1991 | Stephens, Jr. et al. |
| 5,252,479 | A | * | 10/1993 | Srivastava ............... 435/235.1 |
| 5,328,470 | A | * | 7/1994 | Nabel et al. ........... 604/101.03 |
| 5,338,662 | A | * | 8/1994 | Sadri ....................... 435/284.1 |
| 5,368,555 | A | | 11/1994 | Sussman et al. |
| 5,423,778 | A | | 6/1995 | Eriksson et al. |
| 5,443,836 | A | | 8/1995 | Downey et al. |
| 5,498,427 | A | | 3/1996 | Menasche |
| 5,580,558 | A | | 12/1996 | Kitamura |
| 5,684,143 | A | | 11/1997 | Gryaznov et al. |
| 5,792,453 | A | | 8/1998 | Hammond et al. |
| 5,821,235 | A | | 10/1998 | Henning et al. |
| 5,869,230 | A | | 2/1999 | Sukhatme |
| 5,871,464 | A | * | 2/1999 | Tryggvason et al. ........ 604/506 |
| 6,342,214 | B1 | * | 1/2002 | Tryggvason et al. ....... 424/93.2 |

* cited by examiner

Primary Examiner—Manuel Mendez
(74) Attorney, Agent, or Firm—Fay, Sharpe, Fagan, Minnich & McKee, LLP

(57) ABSTRACT

The present invention provides methods and devices for the delivery of pharmaceuticals to target tissues in situ, in vivo, ex vivo, or in vitro. In particular, the methods and devices relate to contacting a target tissue with a pharmaceutical in a re-circulating, oxygenated perfusate solution to provide for effective delivery of the pharmaceutical to the target tissue.

12 Claims, 10 Drawing Sheets

PERFUSION APPARATUS AND METHODS FOR PHARMACEUTICAL DELIVERY

CROSS REFERENCE

Continuing Data

This application is a continuation-in-part of U.S. application Ser. No. 09/167,894, filed Oct. 7, 1998, which is a continuation of U.S. application Ser. No. 08/761,793, filed Dec. 6, 1996 (now U.S. Pat. No. 5,871,464) which is a continuation of U.S. application Ser. No. 08/442,189, filed May 16, 1995 (abandoned) and this application is also a continuation-in-part of U.S. application Ser. No. 08/952,501, filed Mar. 23, 1998, which is a 371 and claims the benefit of the filing date of PCT/IB96/00463, filed May 16, 1996, now WO96/36363. This application also claims the benefit of the filing date of Provisional Application Serial No. 60/142,251, filed Jul. 2, 1999.

FIELD OF THE INVENTION

The present invention relates to methods and apparatus for delivery of pharmaceuticals to target tissues in situ, in vivo, ex vivo, or in vitro.

BACKGROUND OF THE INVENTION

Advances in recombinant-DNA technology have made introduction of therapeutic genes into somatic cells possible (Anderson, Nature 357:455–457, 1992). In recent years, several clinical trials involving human gene therapy have been accepted by regulatory agencies. The initial human gene therapy clinical trials aimed at treating both inherited diseases (such as severe combined immunodeficiency caused by lack of adenosine deaminase in peripheral T-lymphocytes, cystic fibrosis, and familial hypercholesterolemia), as well as noninherited disease such as cancer (Wolfe, Curr. Opinion in Pediatr. 6: 213–219, 1994; Sanda et al., J. Urology 44:617–624, 1994; O'Malley et al., Arch. Otolaryngol. Head Neck Surgery 119:1191–1197, 1993; Engelhardt et al., Nature Genetics 4: 27–34, 1993; Lemarchand et al., PNAS (USA) 89: 6482–6486, 1992; Jaffe et al., Nature Genetics 1:372–378, 1992).

The development of suitable, safe, and effective gene transfer systems is a major goal of research in gene therapy. Thus far, viruses have been extensively used as vectors for gene therapy. (See, for example, Pilewshi et al., Am. J. Physiol. 1995;268(4 pt 1):L657–665; Prince, Pathology 1998;30(4):335–347). For example, retroviruses have been widely used, but they can only target actively dividing cells, and do not readily accommodate large DNA inserts. Adeno-associated viruses are also limited in the ability to accommodate large inserts, yet replication defective adenoviruses have been used successfully to transfer of a variety of genes into cells in culture and in vivo. Adenoviruses can accommodate larger inserts than retroviruses, but extra-chromosomal expression usually lasts only for a few weeks. Herpes viruses have been exploited for specific gene transfer trials into the central nervous system. Herpes viruses can carry large foreign DNA inserts, and may remain latent for long periods of time.

In spite of the availability of replication defective viruses, concerns about the safety and efficiency of such viral vectors have generated interest in the development of non-viral gene transfer systems such as liposome-DNA complexes and receptor mediated endocytosis (Felgner P. L. et al., PNAS (USA) 84: 7413–7417, 1987; Hyde Nature 362: 250–255, 1993; Nu G. Y. J. Biol. Chem. 266: 14338, 1991).

A major hurdle for effective gene therapy is the development of methods for targeting the gene transfer to appropriate target cells and tissues. Ex vivo gene transfer into explanted cultured cells and implantation of the treated cells has been used for the treatment of hematopoietic tissues (U.S. Pat. No. 5,399,346, hereby incorporated by reference), and bronchial epithelial cells in animal model. (Engelhardt et al., Nat Genet 1993;4:27–34) Also, direct injection into brain and lung tumors (Cusack et al., Cancer Gene Ther 1996; 3(4):245–249), intravenous or intra-arterial administration (Schachtner et al., Circ Res 1995; 76:701–708), inhalation (Katkin et al., Hum Gene Ther 1995; 6:985–995), and topical application (Pilewshi et al., Am J Physiol 1995;268(4 pt 1):L657–665) have been used. Major drawbacks to all of these methods are that the transduction is not highly selective, significant amounts of the therapeutic gene containing vector may be needed, and efficiency of the gene transfer is severely limited by the constraints of vector concentration, time of exposure to the target, and effectiveness of the gene transfer vector.

Much research is being conducted to enhance transgene expression in target cells. Gene transfer efficiency has been reported to improve by pretreatment with host barrier properties modificating agents (e.g polidocanol), before vector administration. (Parsons et al., Hum Gen Ther Dec. 10, 1998; 9(18):2661–72). Modification of the host's immune system may enhance the transgene expression in viral mediated gene transfer. (Ghia et al., Transplantation Dec. 15, 1998; 66(11):1545–51) Another method reported to enhance gene transfer efficacy is prolonging the incubation time with the vector and the target cells. (Zabner et al., J. Virol. 1996; 70;6994–7003)

One area of active research is gene therapy into mammalian kidneys, but the results have been disappointing because of poor gene transfer efficiency (Woolf et al., Kidney Int. 43: Suppl. 39: S116–S119, 1993). Moullier et al. showed some adenovirus-mediated transfer of lacZ gene into rat tubular, but not glomerular cells, following a combination of virus infusion into the renal artery and retrograde infusion into the vector (Kidney Int. 45: 1220–1225, 1994). Simple infusion of soluble virus does not appear to be an efficient transfer system. Better results were obtained by Tomita et al., (Biochem. Biophys. Res. Commun. 186: 129–134, 1992), who infused a complex of Sendai virus and liposomes into the rat renal artery in vivo, resulting in marker gene expression in about 15% of the glomerular cells.

Alport syndrome is an inherited kidney disease characterized by progressive hematuria, development of renal failure and frequently also hearing loss (Atkin C L and Gregory M C: Alport syndrome; IN: Schrier W W, Gottschalk C W, eds. Diseases of Kidney, Little Brown, Boston 1993 pp 571–592; Tryggvason K, Heikkilä P: Alport syndrome. In: Jamison L, ed. Principles of molecular medicine, Humana Press Inc.

Totowa N.J. USA 1998 pp 665–668). The only available treatment is hemodialysis and/or kidney transplantation. The underlying cause of the disease is defective structure of the type IV collagen meshwork of the glomerular basement membrane (GBM). This typically results in abnormal thinning and thickening and a basket-weave-like pattern of the GBM. The disease affects about 1:5,000 males (Atkin C L and Gregory M C: Alport syndrome; IN: Schrier W W, Gottschalk C W, eds. Diseases of Kidney, Little Brown, Boston 1993 pp 571–592). About 85% of the cases are caused by mutations in the X chromosomal gene for the type IV collagen α5 chain (Barker, D., Hostikka, S. L., Zhou, J., Chow, L. T., Oliphant, A. R., Gerken, S. C., Gregory, M. C., Skolnick, M. H., Atkin, C. L. and Tryggvason, K.: Identification of mutations in the COL4A5 collagen gene Alport syndrome. Science 248, 1226–1227, 1990, Hostikka S L, Eddy R L, Byers M G, Höyhtyä M. Shows T B. Tryggvason K Identification of a distinct type IV collagen a chain with restricted kidney distribution and assignment of its gene to the locus of X chromosome-linked Alport syndrome. Proc Natl. Acad Sci USA 1990:87:1606–1610, Tryggvason, K Mutations in type IV collagen genes and Alport phenotypes. In: Molecular Pathology and Genetics of Alport Syndrome (Ed. Karl Tryggvason), Karger, Basel, Vol. 117, pp. 154–171, 1996). The less frequent autosomal forms are caused by mutations in the type IV collagen α3 or α4 chain genes located on chromosome 2 (Mochizuki T, Lemmink H H, Mariyama M, Antignac C, Gubler M-C, Pirson Y, Verellen-Dumoulin C, Chan B, Schöder C H, Smeets H J, Reeders S T: Identification of mutations in the_3(IV) and 4(IV) collagen genes in autosomal recessive Alport syndrome. Nature Genet 1994;8: 77–81, Lemmink K K, Mochizuki T, van den Heuvel L P W J, Schröder C H, Barrientos A, Monnens L A H, van Oost B A, Brunner H G, Reeders S T, Smeets J M mutations in the type IV collagen α3 (COL4A3) gene in autosomal recessive Alport syndrome. Hum Mol Genet 1994;3:1269–1273.

Type IV collagen is a basement membrane specific collagen type which is the main structural component of these extracellular structures (Hudson B G. Reeders S T. Tryggvason K Type IV collagen: Structure, gene organization and role in human diseases. Molecular basis of goodpasture and Alport syndromes and diffuse leiomyomatosis. J Biol chem. 1993:268:26033–26036). Similarly to other collagens type IV collagen is a triple-helical protein consisting of three α chains. The collagen α chains have $(Gly-Xaa-Yaa)_n$ repeats, glycine being the only amino acid small enough to fit into the center of the triple helix. The type IV collagen α chains have many interruptions in the Gly-Xaa-Yaa repeat which allows the formation of flexible kinks in the triple-helical molecules. In addition to the collagenous domain, the type IV collagen molecules have noncollagenous globular NCl domain at the carboxyl end, and the aminoterminal 7S domain. Six genetically distinct type IV collagen α chains have been described. The α1(IV) and α2(IV) chains are ubiquitous and are present in triple-helical molecules in a 2:1 ratio (Kühn K Basement membrane-type collagen. Matrix Biol 1994:14:439–455). The other a chains vary in their more restricts tissue distribution. The current understanding type IV collagen synthesis in the renal glomerulus is illustrated in FIG. 5. In the GBM, α1(IV) and α2(IV) are prominent during embryonic development (FIG. 5), but after birth these are replaced by α3(IV), α4(IV) and α5(IV) chains (Miner J H, Sanes J R: Collagen IV (α3, α4, and α5 chains in rodent basal laminae: sequence, distribution, association with laminins, and developmental switches. J Cell Biol 1994p;127:879–891) that, because of high cysteine content (Leinonen A. Mariyama M. Mochizuki T. Tryggvason K. Reeders S T Complete primary structure of the human type IV collagen α4(IV) chain; comparison with structure and expression of the other α(IV) chains. J Biol Chem. 1994;269:26172–26177) are thought to be necessary for forming a stronger, more cross-linked network of triple-helical molecules composed of α3(IV), α4(IV) and α5(IV) chains in a 1:1:1 ratio (Gunwar S. Ballester F. Noelken M E. Sado Y. Ninomiya Y. Hudson B G: Glomerular basement membrane; identification of a novel disulfide cross-linked network of α3, α4 and α5 chain of type IV collagen and its implication for the pathogenesis of Alport syndrome. J Biol Chem. 1998;273:8767–8775)(see FIG. 5). In X-linked Alport syndrome caused by a mutation in the α5(IV) chain gene, the α3(IV) and α4(IV) chains are usually absent from the GBM, even though their genes reside on chromosome 2 (Nakanishi K. Yoshikawa N, Iijima K, Kitagawa K, Nakamura H, Ito H, Yoshioka K, Kagawa M, Sado Y: Immunohistochemical study of α1–α5 chains of type IV collagen in hereditary nephritis. Kidney Int. 1994;46:1413–1412). This is presumably due to intracellular degradation of the chains in the absence of α5(IV) that is essential for the α3:α4:α5 trimer. Instead, the GBM contains embryonic type of collagen IV molecules consisting of al and α2 chains (FIG. 5). However, since these apparently do not provide sufficient mechanical strength to the GBM and sufficient resistance to proteolysis (Kalluri R. Shield III C F, Todd P. Hudson B G Neilson E G Isoform switching of type collagen is developmentally arrested in X-linked Alport syndrome leading to increased susceptibility of renal basement membranes to endoproteolysis. J clin Invest 1997;99:2470–2478), the consequence is deterioration of the structure and development of Alport syndrome.

Alport syndrome is an attractive candidate disease for gene therapy due to its high kidney specificity and because the isolated blood circulation of the kidneys makes them a good target for organ specific gene transfer. The principle of gene therapy of Alport syndrome is depicted in FIG. 5. This requires transfer of the appropriate type IV collagen a chain gene to the endothelial an epithelial cells of the glomerulus, expression of the protein and intracellular assembly of the exogenous recombinant chain into triple-helical molecules together with the endogenous or α3, α4 or α5 chains, and finally, secretion of the protein and incorporation of the protein into the GBM type IV collagen network (see FIG. 5)(Tryggvason K, Heikkilä P, Pettersson E, Tibell A, Thomer P. Can Alport syndrome be treated by gene therapy? Kidney Int 1997;51:1493–1499). For the development of gene therapy of Alport syndrome, we have previously developed an organ perfusion system for adenovirus-mediated gene transfer into renal glomeruli in vivo (Heikkilä P. Parpala T. Lukkarinen O. Weber M. Tryggvason K. Adenovirus-mediated gene transfer into kidney glomeruli using an ex vivo and in vivo kidney perfusion system—first steps towards gene therapy of Alport syndrome. Gene Therapy 1996;3:21–27). Using this procedure we obtained a transfer efficiency up to 85% of pig glomeruli using an adenovirus containing the β-galactosidase reporter gene. Surprisingly, the kidney perfusion method only revealed efficient transfer to glomerular cells, while cells in other regions of the kidney did not take up significant amounts of the virus.

Another active research area is gene therapy into the lung. To date, most gene therapy approaches to both inherited and acquired lung diseases have involved viral or liposome mediated gene delivery via the airway, which provides direct access to lung epithelia. (Griesenbach et al., Gene Ther 1998;5:181–188) At least one drawback of the aerosol delivery, especially in advanced cystic fibrosis (CF), is that the infected mucus layer in bronchioles may impair access to the cell surface. So far, intravascular infusions of the vectors have yielded quite inefficient gene transduction.

There are a variety of diseases that are candidates for somatic lung directed gene therapy, including CF and $_α$1-antitrypsin deficiency, which are the most common inherited diseases having serious pulmonary manifestations. The first reports of in vitro correction of the CF chloride channel defect came in 1990 (Drumm et al., Cell 1990; 62:1227–1233) and in vivo CF gene expression could be established in the airways of mice in 1992. (Rosenfeld et al., Cell 1992;68:143–155) Another candidate for lung directed gene therapy is the surfactant protein B deficiency, an autosomal recessive pulmonary disease, which manifests in neonates and leads to lethal respiratory failure within the first year of life. Gene therapy is also being considered for the treatment of inflammatory and infectious diseases and of cancer of the lung. (Dubinett et al., Hematol Oncol Clin North Am 1998;12(3):569–94)

It would be extremely beneficial to the medical arts to have apparatuses and methods for the efficient administration of gene therapy to target cells and tissues that overcome the limitations inherent to the various gene transfer vector.

SUMMARY OF THE INVENTION

In accordance with an aspect of the present invention, there are provided methods for the administration of pharmaceuticals to targets for functional use. The term "pharmaceutical," as used herein, includes chemical drugs, protein drugs, nucleic acid drugs, combination chemical/protein/nucleic acid drugs, and gene therapy vectors.

The term "functional use," as used herein, includes therapeutic treatment, prophylaxis, and/or production of recombinant proteins in vivo. The term "functional use" also includes the disruption of endogenous gene expression including the use of antisense, triplex forming, catalytic and otherwise disruptive pharmaceuticals. The term "functional use" also includes the expression of recombinant proteins in target tissues, whether of endogenous or exogenous origin. The term "target," as used herein, includes cells, tissues and/or organs.

The term "gene therapy vector" is meant to include nucleic acid constructs which are single, double or triplex stranded, linear or circular, that are expressible or nonexpressible constructs which can either encode for and express a functional protein, or fragment thereof, or interfere with the normal expression of a target gene, gene transfer and/or expression vectors.

The administration of pharmaceuticals may take place where the target is in situ in a living subject. The administration may also take place wherein the target is first removed from a subject, manipulated ex vivo, and returned to the original or, alternatively, to a second recipient subject. In a preferred embodiment, the target is situated such that the circulation of the blood supply into and out of the target is relatively isolated. In a most preferred embodiment, the blood circulation into and out of the target is mostly via a single, or readily identified entering arteries and exiting veins. There are of course certain amounts of limited leakage due to small blood and lymphatic vessels.

The methods of the instant invention allow for a prolonged period of administration of pharmaceuticals to a target by way of re-circulating a pharmaceutical containing solution through the target such that a perfusion effect occurs. The methods of the instant invention allow for prolonged administration because of the unique use of the perfusion method and the oxygenation of the pharmaceutical containing solution. In one embodiment, the perfusion apparatus and target forms a closed system whereby the pharmaceuticals are administered at a starting concentration and not adjusted during the time course of treatment. In another embodiment, the pharmaceutical concentration is periodically adjusted so as to maintain or otherwise alter the concentration of pharmaceutical in the solution, or additional pharmaceuticals are added. In a preferred embodiment, the solution does not require replenishment during the course of treatment. In another embodiment, the solution volume can be replenished as leakage or other forms of loss occur during the course of treatment. (The term "solution," as used herein refers to the medium in which the pharmaceutical is suspended, dissolved or otherwise maintained for delivery to the target, aka. the perfusate, and includes blood, serum, plasma, saline, and/or buffered solutions.) In a preferred embodiment, 350 ml of perfusate contains red blood cells (around 17% of hemocrit value), and can include about 25,000 IU heparin, about 20,000 IU penicillin and about 20,000 µg streptomycin in Krebs-Ringer solution in addition to the pharmaceutical.

The instant invention also provides methods for delivering viral vector gene therapy pharmaceuticals to a mammalian target tissue comprising contacting the mammalian target tissue with the viral vector gene therapy pharmaceutical in a re-circulating, oxygenated perfusate solution, where said solution is held at about 37° C., such that there is effective delivery of the viral vector gene therapy pharmaceutical. In a preferred embodiment, the mammalian target tissue is selected from kidney, liver, mammary glands, spleen, and lung.

In another embodiment, the present invention provides methods for the extended delivery of a pharmaceutical to mammalian kidney tissue comprising contacting the mammalian kidney tissue with the pharmaceutical in a re-circulating, oxygenated perfusate.

The instant invention further provides improved methods for gene therapy of kidney disorders, comprising contacting the kidney of a patient with a kidney disorder with an amount effective for treatment of the disorder of a gene therapy pharmaceutical for treatment of the disorder, wherein the improvement comprises contacting the patient's kidney with the viral vector gene therapy pharmaceutical in a re-circulating, oxygenated perfusate solution.

In a more particular embodiment, the invention provides for treatment of Alport syndrome in a patient by gene therapy, comprising contacting the kidney of a patient with Alport syndrome with recombinant α5(IV) chain, obtained from human type (IV) collagen α5 cDNA, using a re-circulating, oxygenated perfusate solution.

The instant invention also provides for a perfusion apparatus functionally connected by a perfusate transfer system comprising, (a) a reservoir for perfusate, (b) means for propelling the perfusate through the apparatus, (c) means for oxygenation of the perfusate, (d) means for connecting the apparatus to and from the target.

The reservoir for the perfusate can be any container that can be sterilized and used to collect perfusate from the target. The reservoir is connected to the means for transporting the perfusate through the system by means of tubing. While perfusion may occur at room temperature of 20° C., in a preferred embodiment, the perfusion occurs at 37° C. Thus, in practice, the perfusate reservoir can be maintained at any desired temperature via, for example, a water bath.

In an embodiment where the means for propelling the perfusate is a peristaltic pump, the tubing is preferably silicone or other such suitable pliable tubing. Where the means for propelling the perfusate is a peristaltic pump, no contact is made between the perfusate and any part of the pump directly. In the case where a pump with, for example an impeller blade is used, then the perfusate comes into direct contact with a part of the pump. In the usual configuration using a peristaltic pump, the tubing from the reservoir passes through the pump and connects with the means for oxygenating the perfusate.

The means for oxygenating the perfusate can be any form of artificial lung, or aeration device such that the perfusate is oxygenated without overt agitation and subsequent frothing. In one embodiment the means for oxygenating the perfusate is a membrane lung which consists of a length of semi-permeable tubing packed into a gas chamber into which is circulated oxygen rich gas, for oxygenating the perfusate as it pass through the length of tubing. In a preferred embodiment, the membrane lung contains about 8 meters of silicon tubing of approximately 1.47 mm inside diameter, and the gas circulated in the chamber is carbogen gas (comprised of 95% oxygen, 5% carbon dioxide).

In general, the target is cannulated and connected to tubing connecting from the means for oxygenating the perfusate, and leading to the perfusate reservoir. In one configuration, the perfusate is pumped from a reservoir, through a means for oxygenating the perfusate, into the target, through the target, and back into the reservoir. The location of the pumping means in relation to the other components can be varied. The number of each component can also be varied.

Thus the instant invention provides for a method of administering a pharmaceutical to a target whereby the target is mostly isolated and continuously perfused with a perfusate containing the pharmaceutical, and said perfusate is recirculated and oxygenated. The instant invention provides for an apparatus for the administration of pharmaceuticals to a target comprising a perfusate reservoir, means for pumping the perfusate, means for oxygenating the perfusate, and means for connecting the components to one another, and with the target. In a preferred embodiment the re-circulating perfusion apparatus comprises a perfusate reservoir receiving efflux perfusate from the target, connected with silicone tubing passing via a peristaltic pump to a membrane lung, said membrane lung comprising about 8 m of approximately 1.47 mm inner diameter silicone tubing immersed in a circulating gas chamber filled with carboxygen gas, connected by tubing and a catheter to a target.

BRIEF DESCRIPTION OF THE DRAWINGS

FIG. 3 shows the expression of beta-galactosidase in porcine kidney following in vivo perfusion with AdCMV-lacZ virus.

FIG. 4 shows the expression of beta-galactosidase in isolated human glomeruli infected with AdCMVlacZ virus.

DETAILED DESCRIPTION OF THE PREFERRED EMBODIMENTS

Figure 1:
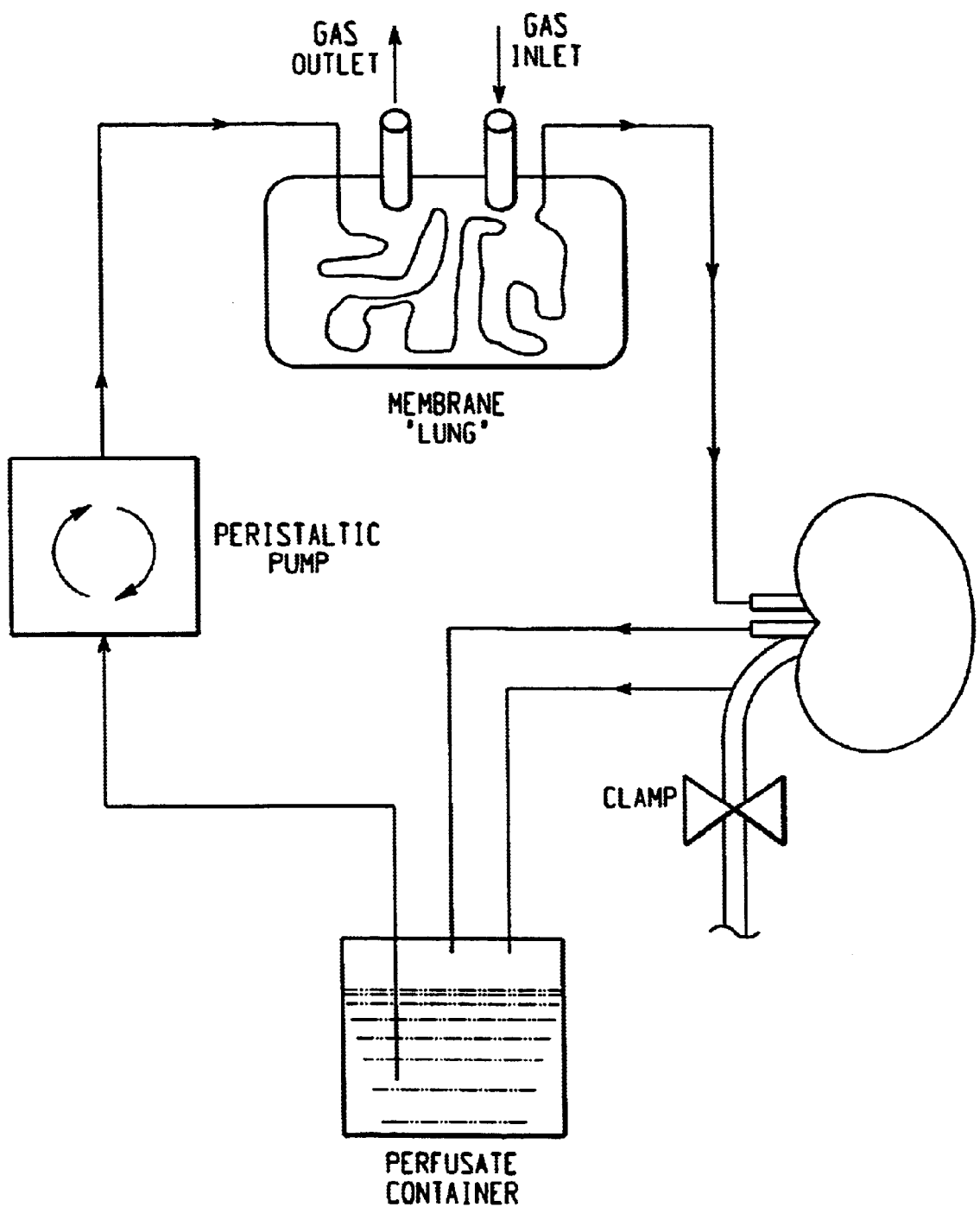
FIG. 1 is a drawing of the perfusate re-circulation apparatus connected to a kidney.

As described above, the instant invention provides for methods and means for greatly enhancing the efficiency of phamaceuticals for functional use, in particular with the use of gene therapy vectors.

The following experiments illustrate surgical ex vivo and in vivo kidney and lung perfusion using the methods and apparatus of the instant invention to effect highly efficient adenovirus-mediated gene transfer into glomerular and lung epithelial cells, using pigs as the experimental animal. This method of gene therapy may have specific application to the treatment of kidney diseases such as Alport syndrome (Barker et al., Science 248:1224–1227, 1990; Tryggvason et al., Kidney Int. 43:38–44, 1993; Mochizuki et al., Nature Genetics 8:77–82, 1994), and lung diseases such as cystic fibrosis, $_\alpha$1-antitrypsin deficiency, surfactant protein B deficiency, and for the treatment of inflammatory and infectious diseases and of cancer of the lung. (Drumm et al., Cell 1990;62:1227–1233; Rosenfeld et al., Cell 1992;68:143–155; Dubinett et al., Hematol Oncol Clin North Am 1998;12(3):569–94).

The following examples show that gene transfer into kidney cells after intra-arterial injection was highly insignificant. Even the use of high pharmacological amounts of a number of vasodilative agents does not noticeably improve the uptake of virus into the target kidney cells. In contrast, the organ perfusion system showed efficient gene transfer into glomeruli using both ex vivo and in vivo perfusion. The results of up to 80% transfer (ex vivo), or 75% transfer (in vivo), are in dramatic contrast to the results obtained with other methods of transfer into the kidney.

The following examples further show successful adenovirus-mediated gene transfer into the lung by using the apparatus and methods of the invention. The gene transfer by this method is highly organ specific but seems not to be very cell type specific. Bronchial epithelial and alveolar epithelial cells, which are essential to expression of the CF gene or surfactant protein B gene, showed transgene expression.

The perfusion system of the instant invention is applicable for gene transfer and pharmaceutical administration into a number of organs. The apparatus and methods are applicable when the target organ has a suitable blood circulation system. The flood of perfusate is most efficient if the organ has one end artery but it is not impossible to accomplish even though there are more than one. Organs that lend themselves to such methods include the kidney, liver, mammary glands, spleen and lung. It is even possible to apply the instant methods to isolated segments of blood vessels. Perfusion pressure should be monitored during perfusion to prevent any pressure damage in the organ.

Where the pharmaceutical agent is a gene therapy vector, the construct may functionally encode for endogenous or exogenous proteins, which can then be expressed in the target after treatment. Such gene transfer will allow for the expression of various proteins by the target tissues.

The most obvious benefit of the instant perfusion system and methods is the enhanced efficiency, the target specificity for gene transfer, and the possibility of using only a small amount of vector material. Furthermore, extracorporeal perfusion systems diminish the risk of administering a large amount of foreign genetic material into the general circulation of the subject, especially important for immunocompetent individuals.

In addition, the present application provides for methods and means for treatment of Alport syndrome by gene therapy. The basic disorder of this disease is an GBM abnormal network made of triple-helical type IV collagen molecules consisting of α3(IV), α4(IV) and α5(IV) chains. Mutations in any of the respective genes can lead to the disease.

Gene therapy of Alport syndrome aims at transfer of a corrected type IV collagen a chain gene into renal glomerular cells responsible for production of the GBM. The prerequisites for gene therapy of Alport syndrome include: (1) availability of an appropriate gene delivery system into cells of kidney glomeruli; (2) expression of the delivered type IV collagen gene in those cells; (3) proper modification and folding of respective a chain facilitating intracellular association into normal type IV collagen trimer and; (4) incorporation of those trimers in the GBM, which would further restore the structure and function of the GBM. We have previously demonstrated the possibility of targeting expression of foreign genes into cells of the renal glomeruli in vivo using adenovirus containing a reporter gene (Heikkilä P. Parpala T. Lukkarinen O. Weber M. Tryggvason K. Adenovirus-mediated gene transfer into kidney glomeruli using an ex vivo and in vivo kidney perfusion system—first steps towards gene therapy of Alport syndrome. Gene Therapy 1996;3:21–27). The results of this study represent two significant steps forward towards gene therapy of Alport syndrome. First, it was demonstrated that one can use adenovirus to produce recombinant α5(IV) chain in cultured human cells so that this chain is incorporated into triple-helical type IV collagen molecules containing also α3 and α4 chains, as does normal type IV collagen of the GBM. Second, the adenovirus-mediated expression of the recombinant human α5(IV) chain in pig kidneys in vivo resulted in production of the polypeptide chain which also was deposited into the extracellular matrix.

Type IV collagen composed of α3, α4 and α5 chain is predominant in the renal GBM shown in biochemical assays (Gunwar S. Ballester F. Noelken M E. Sado Y. Ninomiya Y. Hudson B G: Glomerular basement membrane; identification of a novel disulfide cross-linked network of α3, α4 and α5 chain of type IV collagen and its implication for the pathogenesis of Alport syndrome. J Biol Chem. 1998;273:8767–8775) or indirectly by localization of these three chain in the GBM using chain specific monoclonal antibodies (Nakanishi K. Yoshikawa N, Iujima K, Kitagawa K, Nakamura H, Ito H, Yoshioka K, Kagawa M, Sado Y: Immunohistochemical study of α1–α5 chains of type IV collagen in hereditary nephritis. Kidney Int. 1994;46:1413–1412). In this study the recombinant human α5(IV) chain expressed in human fibrosarcoma cell line was associated with α3(IV) and α4(IV) chains but not the α1(IV) or α2(IV) chain of type IV collagen as shown by immunoprecipitation. Although the α3(IV) and α4(IV) chains are expressed at very low level in HT1080 cells they were easily detectable in immunoprecipitate with monoclonal antibodies. Also, a minor band in the lane stained with an α2(IV) antibody was visible. The faint staining for the α2(IV) chain is considered insignificant, because the α2(IV) chain is expressed in these cells in considerably higher amounts compared to that of the α3(IV) and α4(IV) chains. However, it is possible that minor amounts of α2(IV) chain can be associated to the network composed of α3(IV), α4(IV), and α5(IV) chains by noncovalent interactions as shown by Gunwar et al. (1998). The association of α5(IV) and α6(IV) chains could not be detected in this cell line, because HT1080 cells do not produce the α6(IV) chain. Since immunoprecipitation of the recombinant α5(IV) chain selectively brings down α3(IV) and α4(IV) chains from the HT1080 culture media, these three chains are most likely present in the same triple-helical molecule. The chain composition of these trimers is likely to be (α3, α4, α5) which is the chain composition found in the GBM (Gunwar et al. 1998). These findings have been obtained in cell culture conditions, but in principle, this should work in the same way in vivo when transferring the α5 chain into kidney in order to treat kidney failure in Alport syndrome.

The adenoviral gene transfer into kidney in vivo resulted in expression of human α5(IV) chain in swine kidney glomeruli. This was detected both in mRNA and protein level by in situ hybridization and by indirect immunofluoresence, respectively. The gene delivery was successful mainly into glomerular epithelial cells which are indeed the target cells in the gene transfer in Alport syndrome because the type IV collagen α5 chain is expressed in these cells normally. Apparently, the recombinant α5(IV) chain was able to assemble with the endogenous porcine α3(IV) and α4(IV) chains and secreted out of the cells because a linear staining pattern resembling the GBM staining were found in glomerulus in perfused kidney. This indicates that the recombinant α5 chain can incorporate into the GBM in vivo.

Theoretically, the incorporation of collagen molecules into extracellular matrix occurs only if the respective collagen trimer are formed. Therefore, the localization of the recombinant α5(IV) chain in the GBM indicates formation of type IV collagen triplex. The probable composition of these trimers are α3:α4:α5 because in accordance of current understanding trimers composed of these chains are predominant in the GBM. However, the direct evidence of presence of the triple-helical collagen molecules containing the recombinant α5(IV) chains in the GBM has to be verified by immunoelectronmicroscopy and by biochemical analysis of the GEM from the treated kidney.

According to the present invention, two functionally important prerequisites for gene therapy of Alport syndrome have been demonstrated. First, the recombinant α5 chain of type IV collagen is capable of assembling with the α3(IV) and α4(IV) chains into triple helical collagen molecules. Secondly, the recombinant α5(IV) chain introduced into renal glomerular cells in vivo was shown to deposit into the GBM. These results together with the previous development of alomerulus specific gene transfer method strongly imply that Alport syndrome can be treated by gene therapy.

The following examples illustrate certain embodiments of the instant invention and are meant by way of illustration and not limitation.

EXAMPLE 1

Materials and Methods

Reporter gene virus construct: A replication defective recombinant adenovirus (AdCMVlacZ; Dr. James Wilson, Wistar Institute, U. Penn.) containing the cytomegalovirus promoter and E. coli beta-galactosidase gene as a reporter gene was used as the gene transfer vector (Engelhardt et al., supra.) The vector has been deleted of sequences in the E3, E1A and E1B regions, impairing the ability of this virus to replicate and transform non-permissive cells (Hurwitz et al., (PNAS (USA) 82: 163–167, 1985). Adenoviral stocks of recombinant virus were prepared and purified through double CsCl banding (Engelhardt et al., supra.). Titers of viral stocks were determined by plaque assay using 293 human embryonic kidney cells (ATCC CRL1573). The viral preparations were stored in 10 mM Tris-HCl, 10% glycerol at −70° C. until use. The viral preparations were tested for replication competence by extended cultivation on HeLa cells. Expression of the reporter gene was used to identify cells where successful transduction had occurred.

Experimental animals: Experimental animals were young 22–35 kg farm pigs which were treated according to institutional guidelines. In this experiment, operative gene transfer trials were made to 16 animals. The animals were under general anesthesia during the operation. Azaperon (Stresnil) (4 mg per kg) was first administered as intramuscular injection. For induction, medetomidine (Domitor) (80 µg per kg), ketamin (Ketalar) (4 mg per kg) and atropine (Atropin) (0.05 mg per kg) were given intramuscularly. Thiopenthal (Hypnostan) (5 mg per kg) was then given intravenously, the animal was intubated, and the anesthesia was continued under a combination of nitrous oxide-oxygen (1:1) and 1.5% enflurane (Efrane).

EXAMPLE 2

Cultured Human Cells: Human endothelial cells, prepared from the iliac vein and artery of organ donors, were grown in M119 medium supplemented with 20% fetal calf serum (FCS), 100 IU/mL penicillin, 100 µg/ml streptomycin and 30 µg/ml endothelial cell growth factor (Sigma). Mesangial cells were isolated from human glomeruli and identified by light microscopy, based on their typical smooth muscle cell-like morphology, and by other immunohistochemical markers (Holthofer et al., Lab. Invest. 65: 548–557, 1991). The mesengial cells were grown in RPMI medium supplemented with 10% FCS, 100 µg/ml penicillin and 100 µg/ml streptomycin. In addition, a supplement of insulin (25 µg/ml), transfernin (25 µg/ml) and selenium (25 g/ml) (SIGMA) was added to the culture medium.

Isolation of human kidney glomeruli: Intact human glomeruli were prepared from renal cortex of histologically normal portions of the non-involved kidney poles of tumor nephrectomy specimens. The glomeruli were isolated by a standard three-stage sieving method (Misra, Am. J. Clin. Pathol. 58: 135–139, 1972; Tryggvason et al., Nephron 15: 62–68, 1975), by passing renal cortex tissue sequentially through stainless steel sieves of sizes 250, 210 and 75 µm. The smallest pore size retained an almost pure glomerular fraction, which was transferred to six-well plastic plates. The glomeruli were cultured in RPMI1640 medium supplemented with 100 µg/ml penicillin, 100 µg/ml streptomycin, 10% FCS, 5 µg/ml insulin, 5 µg/ml transferrin and 5 ng/ml selenium.

In vitro gene transfer into cell lines and isolated glomeruli: Cultured human endothelial or mesangial cells were infected with the recombinant virus in a medium containing 2% FCS at multiplicity of infection (MOI) of 1 or 10 per cell. Following a 2 hour incubation, the medium was changed to complete culture medium, and the cells were grown for an additional 72 hours and stained with X-gal (5-bromo-4-chloro-3 indolyl beta-galactopyranoside) to study the transfer and expression of the lacZ reporter gene.

The isolated glomeruli were infected with MOI $10^3$–$10^7$ per single glomerulus by incubating the glomeruli with the virus in the supplemented culture medium in the presence of 1% FCS. Ten mM Tris was used as a control. Following 6 or 16 hours of incubation, the glomeruli were rinsed with fresh medium to remove the remaining virus and cultured in complete medium containing 20% FCS. The glomeruli were stained cytochemically three days after infection by adding 1 mg/ml X-gal into the culture medium. Blue beta-galactosidase staining was usually visible after a 2 hour incubation at 370° C.

Results

Adenoviral gene transfer into cultured cells and isolated glomeruli: Primary cultures of human endothelial and mesangial cells that were exposed for two hours to recombinant virus exhibited strong staining for the expression of the lacZ reporter gene (data not shown). Exposure of the cells to virus at an MOI of 100 for 24 hours resulted in expression of the reporter gene in the majority of the cells with no apparent changes in cell morphology. Expression of the lacZ gene appeared about 8 hours following addition of the virus.

The isolated human glomeruli, some of which had lost the Bowman's capsule, could be maintained viable in culture for several days without losing their morphology. During this period, virus infection was carried out and gene transfer efficiency measured. At an MOI of about 1000 virus per glomerulus, expression of the lacZ gene was observed in practically all glomeruli, with all cell types showing positive staining reactions (FIG. 2).

Figure 2:
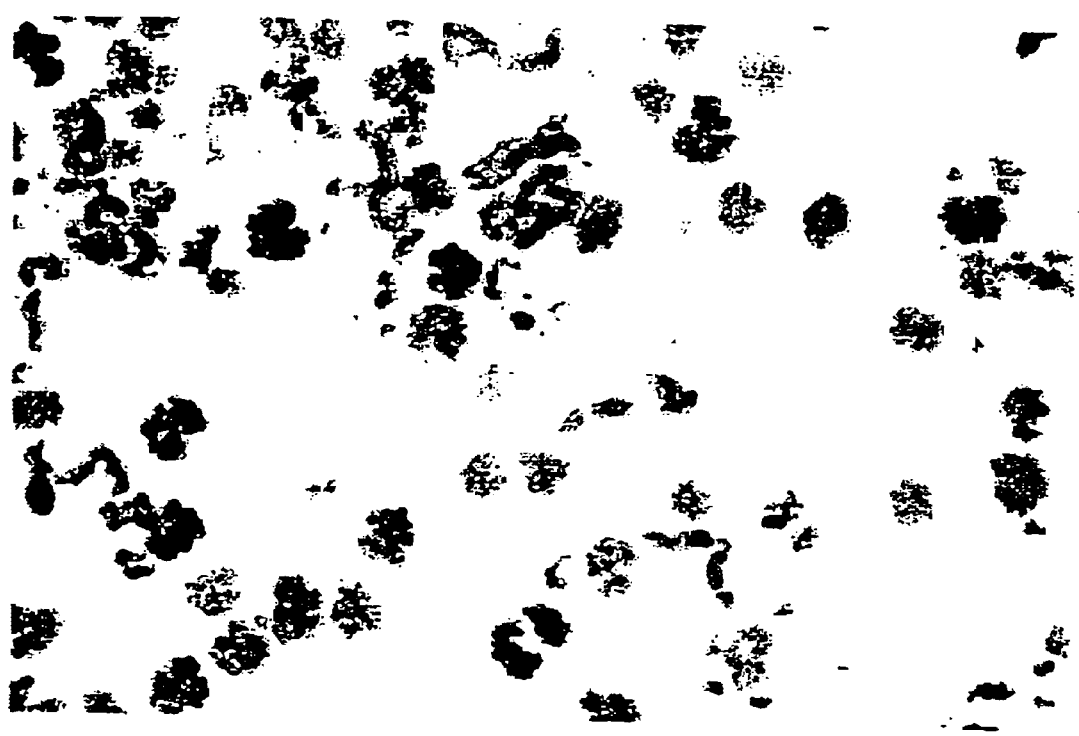
FIG. 2 shows the expression of beta-galactosidase in porcine kidney following ex vivo perfusion with AdCMV-lacZ virus.

FIG. 2 shows cryosections of the explanted kidney samples stained with X-gal and HE. The sections show expression of the beta-galactosidase in isolated human glomeruli infected with AdCMVlacZ virus. The glomeruli were infected with the virus for about 6 hours, incubated without virus for 12 hours, and then stained with X-gal. Most of the glomeruli exhibited intense expression that appeared to involve all cell types of the glomerulus.

EXAMPLE 3

Animals and Histological Staining: as described in Examples 1 and 2.

Intra-arterial Infusion: The virus vector was injected into the renal artery during laparotomy during these tests. Eleven animals were operated on. In the first experiment, 2.5 ml ($2\times10^9$ pfu) of adenoviral preparation was injected through a 0.1 mm butterfly needle directly into the anterior branch of the left renal artery. The animal was sacrificed on the third postoperative day, and nephrectomy was made. Kidney samples were taken for histological examination, and expression of the lacZ gene was examined following staining with X-gal. Because the infusion was made to the lower pole of the kidney, the upper pole was used as a control. Nine of the eleven animals were operated according to a similar scheme as above, except that the vasodilative pharmacological agents were infused intra-arterially into the anterior branch of the renal artery shortly prior to infusion of the virus preparation, in an attempt to diminish the potential vascular resistance in the kidney. Five vasodilative agents were used in different trials: papaverin, alprostadil, enalapiril, verapamil and lidocain. One animal was treated as a control by infusing 10 ml of saline into the renal artery before the viral infusion. The amount of virus injected in these trials was $4\times10^9$ pfu in 8 ml 0.9% saline.

Histochemical analysis: Efficiency of adenoviral gene transfer was monitored by analysis of lacZ gene expression on cryosections. Sections of 5 µm thickness were first fixed for 10 minutes in 4% gluteraldehyde in PBS. Following extensive washings with 1×PBS, the sections were incubated in a detergent solution containing 0.01% sodium deoxycholate, 0.02% NP40 and 2 mM magnesium chloride in PBS for 10 minutes. The sections were incubated in an X-gal solution (detergent solution containing 5 mM potassium ferricyanide, 5 mM potassium ferrocyanide and 1 mg/ml X-gal for 3 hours overnight at 37° C.), and subsequently counterstained with PAS. Possible cytotoxic effects of the virus were evaluated by histological examination of formaldehyde-fixed paraffin embedded tissue sections after PAS-hematoxylin staining.

Results

Gene transfer by infusion into kidney in vivo: These experiments did not lead to successful gene transfer into kidney cells. LacZ gene expression was observed in only a few scattered cells in the kidney cortex, and no signs of expression were seen in the glomeruli (data not shown). Use of vasodilative agents immediately prior to injection of the virus had no visible effect on the efficiency of gene transfer. Even use of up to three consecutive injections at 2 minute intervals did not markedly increase the efficiency of gene transfer (data not shown).

EXAMPLE 4

Animals and Histological Staining: as described in Examples 1 and 2.

Kidney perfusion system: In order to extend the time available for infection of target kidney cells by the virus vector, an apparatus was developed which provided a closed-circuit perfusion system for the continuous circulation of virus solution in the intact kidney in vivo and ex vivo. This system, as shown in FIG. 1, consists of a reservoir for the perfusate, a pump, and an artificial membrane lung connected to the kidney to be perfused, all connected by 3 mm inside diameter silicon tubing. The reservoir for the experiment was a 300 ml glass bottle container placed in a 37° C. water bath. The peristaltic pump was from a portable organ fixation perfusion machine (PF-3 A; Gambro) with a flow rate (rpm) control. The membrane lung consists of 8 m of 1.47 mm inside diameter silicon tubing in a 2000 ml glass container gassed with carbogen (95% oxygen, 5% carbon dioxide) at a pressure of 15 mm Hg, according to Hamilton et al. (J. Libid. Res. 15:182–186, 1974). The kidney was attached to the perfusion system by carmulating the renal artery with a 14 G cannula and the renal vein with a 12 G cannula. The venous and ureter effluents were collected directly into the reservoir. The perfusate had a total volume of 350 ml and contained previously separated red blood cells at a hemocrit value of 17% in Krebs-Ringer solution. Additionally, 25,000 IU heparin and antibiotics were added. For ex vivo perfusion of explanted kidneys, the perfusate also contained 20,000 IU penicillin and 20,000 µg streptomycin as antibiotics, and 5 ml of an MEM amino acid solution. For the in vivo perfusions, the perfusate contained 250 mg cefuroxim as an antibiotic. No direct measurement of perfusion pressure in the kidney was made. To circumvent this problem, the flow rate was adjusted to enable adequate diuresis. The pH and oxygen saturation in the perfusate was measured using routine laboratory "blood gas" analysis of the perfusate.

Kidney perfusion ex vivo: Before connecting the kidney to the perfusion system, a 10 ml lidocain-heparin solution (190 mg lidocain+5,000 IU heparin) and 0.9% saline were infused through the renal artery until the venous effluent was clear. The adenovirus preparation (1×10$^{11}$ pfu in 20 ml Krebs-Ringer solution) was then infused into the arterial inlet, and the perfusion was immediately initiated. The flow rate was set at 100–200 m/min. Diuresis and extraction of virus into the urine were measured throughout the perfusion period.

A total of four kidneys were perfused ex vivo, the average perfusion time being 12 hours. Following the experiments, tissue samples were taken for histologic analysis as described above.

Kidney perfusion in vivo (in situ): Kidneys of three animals were perfused in vivo via laparotomy. The animals were given prophylactic antibiotic (750 mg cefuroxim) intravenously prior to the operation, and 250 mg cefuroxim was added to the perfusate. While the kidney was connected to the perfusion system, it was isolated from the systemic circulation by clamping the renal artery and vein proximally. The ureter was also clamped and ureterostomy was made to collect the effluent into the perfusate and to monitor diruesis. Since perfusion pressure in the kidney could not be measured directly, the flow rate was constantly maintained at 100–120 ml per minute. Diuresis was considered an indicator of sufficient perfusion pressure. In vivo perfusions were carried out for 60 or 120 minutes. Hydrocortisone (50 mg) was administered intramuscularly after the operation. Two animals were sacrificed on the fourth postoperative day and the appropriate kidney was removed for histological examination. One animal was maintained for up to three weeks postoperatively, renal biopsies being taken on days 14 and 21 after which the animal was sacrificed.

Results

Gene transfer by kidney perfusion ex vivo: Perfusion of explanted kidneys with adenovirus at room temperature for up to 17 hours did not result in effective gene transfer to kidney cells (data not shown). In contrast, when perfusion was carried out at 37° C. for 12 hours, marked gene transfer could be seen in glomerular cells. By histologic examination, lacZ gene expression was observed in approximately 80% of the glomeruli, and in several glomeruli most mesangial and endothelial cells as well as epithelial podocytes appeared to be positive (FIG. 3). However, only little staining was seen in endothelial cells of blood vessels elsewhere in the kidney, and epithelial cells of the tubuli did not exhibit any staining.

Figure 3A:
FIG. 3A is at 21×magnification.
Figure 3B:
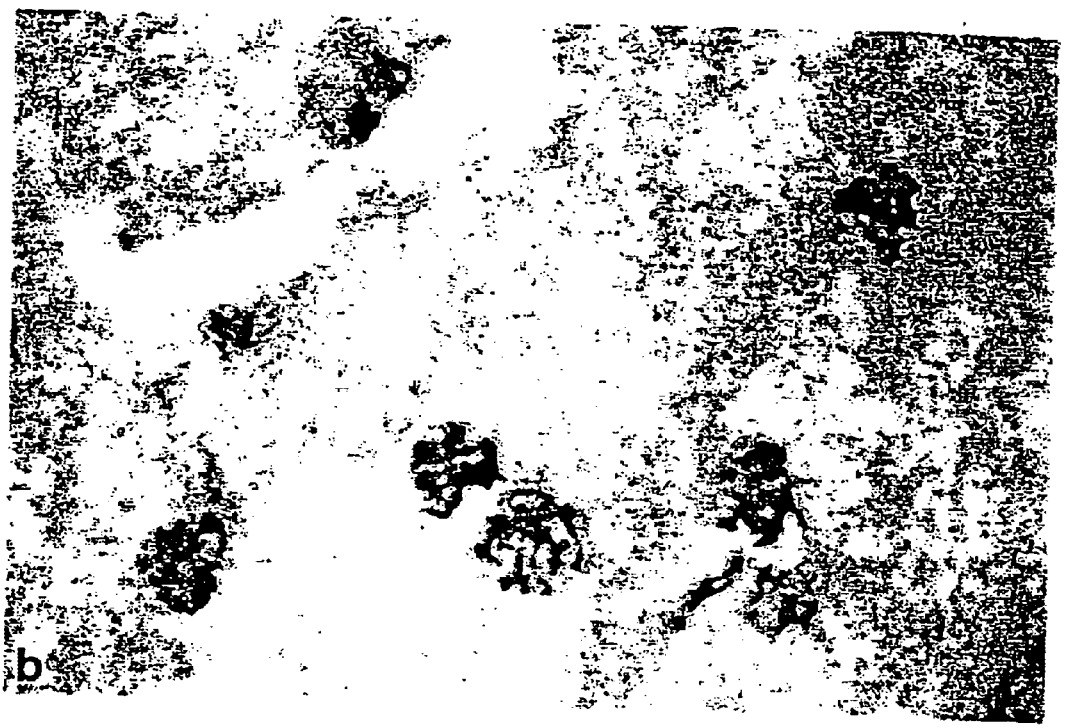
FIG. 3B is at 86× and FIG. 3C is at 214×magnification.
Figure 3C:
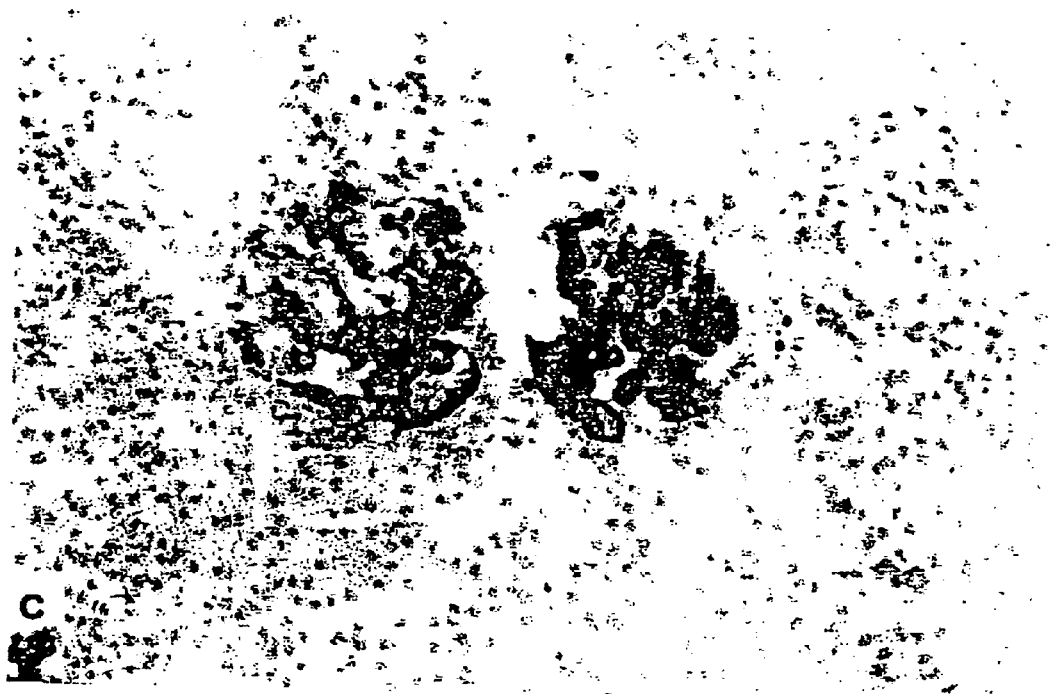

FIG. 3 shows the expression of beta-galactosidase in porcine kidney following ex vivo perfusion with AcCMV-lacZ virus. FIG. 3(A) shows the intense beta-galactosidase expression of staining in a large proportion of the glomeruli, while little if any staining was seen in other regions of the kidney (Magnification is 21×). FIG. 3(B) shows staining for beta-galactosidase in mesangial, endothelial and epithelial cells of the glomeruli, while the cells of the Bowman's capsule are negative (Magnification is 86×). FIG. 3(C) shows the expression of beta-galactosidase in two individual glomeruli. (Magnification 214×).

Gene transfer into kidney by perfusion in vivo: The first in vivo perfusion was carried out for 60 minutes, diuresis being normal during that period. Four days postoperatively, lacZ gene expression was seen predominantly only in glomerular cells (FIG. 4). Expression was found in 9 to 45% of the glomeruli, the mean value being 27% as determined from cross-sections from experimental animals. Within the glomeruli themselves, between 2 and 50% of the cells were estimated to exhibit expression. Expression was not observed in cells of other segments of the kidney, except for some vascular endothelial cells.

Other in situ perfusions were performed for 120 minutes. There was marked polyuria, with diuresis being about 800 ml during the first hour and 1200 ml during the second hour. Four days later, lacZ gene expression was observed in 23 to 75% of the glomeruli, the mean being 58% depending upon the section. In individual glomeruli, expression was seen in most mesangial and endothelial cells, as well as in the epithelial podocytes. In certain segments, all glomeruli appeared to be positive, with seemingly all cells exhibiting expression (FIG. 4). In this experiment, expression was only seen in scattered endothelial cells elsewhere in the vascular system and epithelial cells of proximal and distal tubuli were negative.

Figure 4A:
FIG. 4A is at 21×magnification.
Figure 4B:
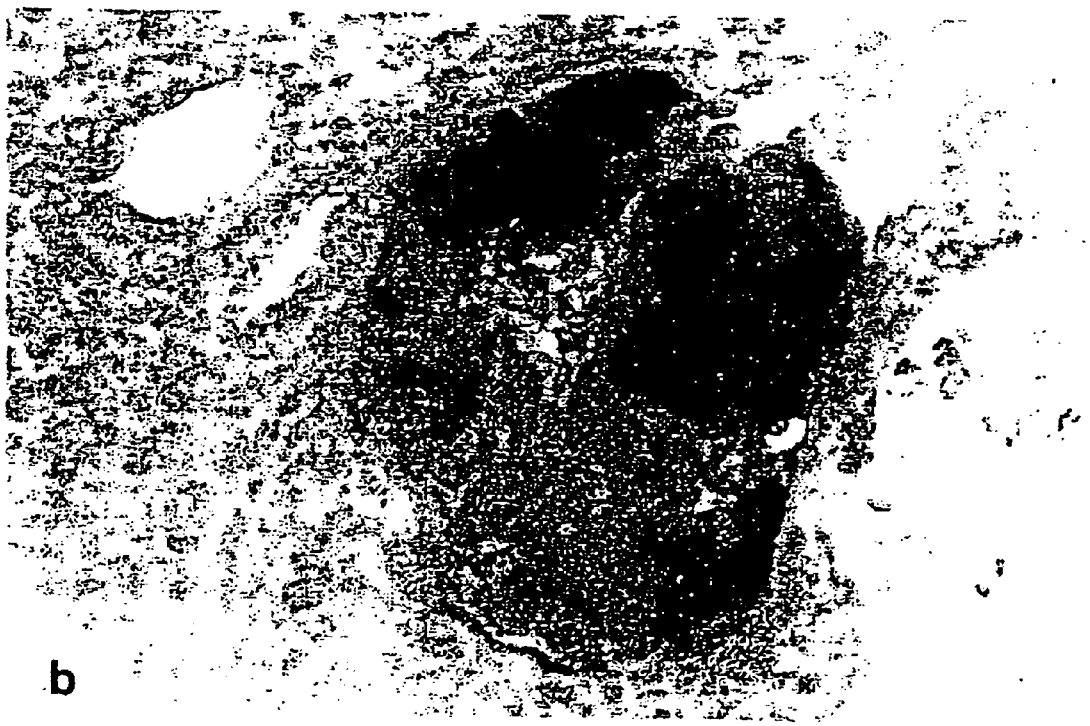
FIG. 4B is at 429× magnification.
Figure 5:
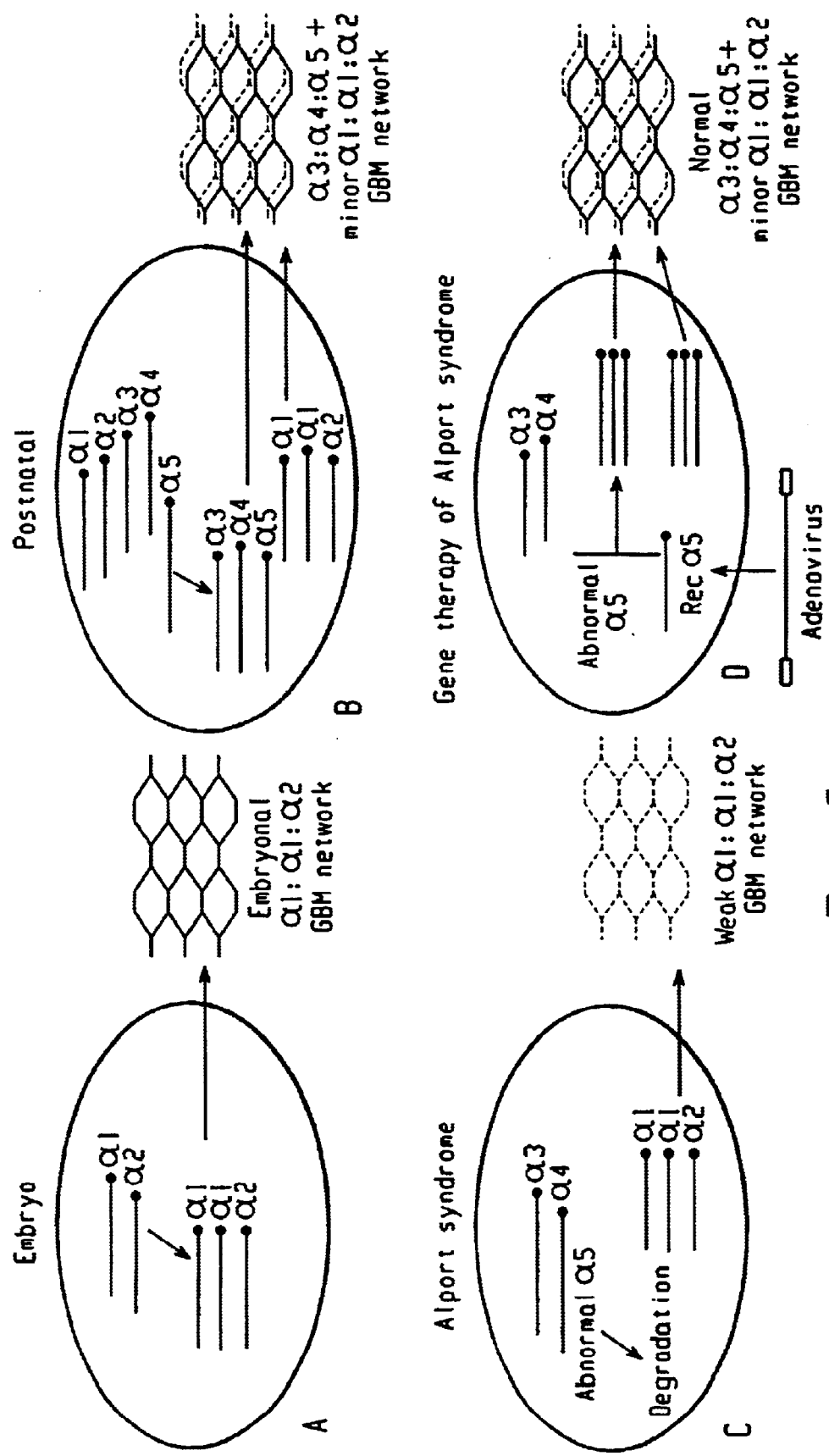
FIG. 5 depicts an illustration of type IV collagen synthesis and incorporation into the GBM network in embryonic, adult and Alport syndrome kidney.
Figure 6A:
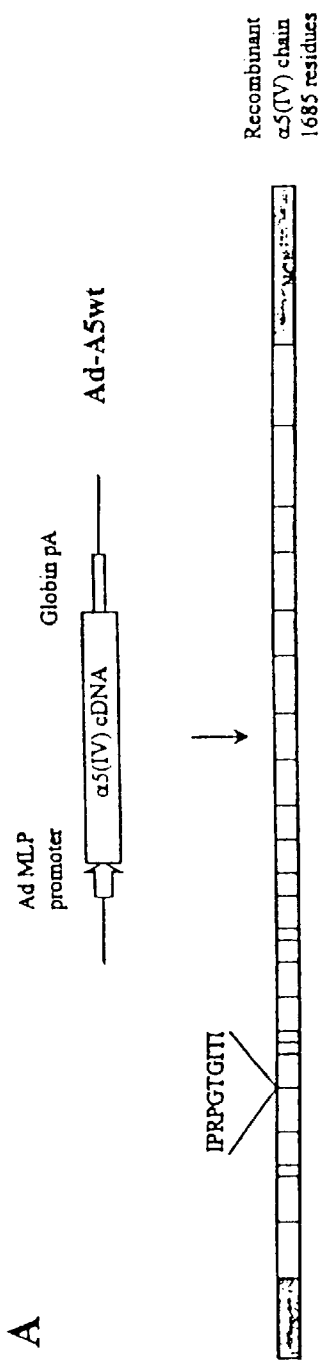
FIGS. 6A and 6B depict two adenovirus constructs expressing human α5(IV) collagen chains and schemes of the respective α5(IV) polypeptide chains.
Figure 6B:
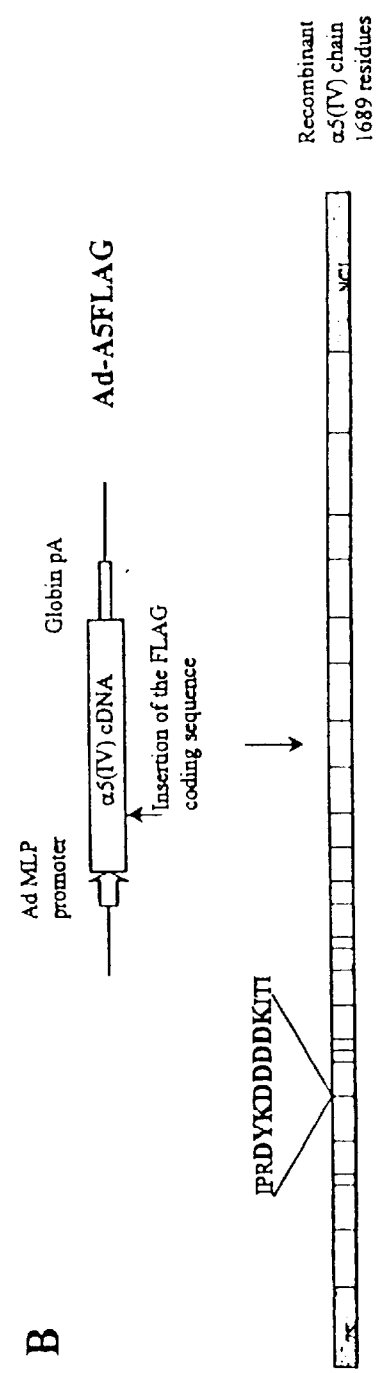

FIG. 4 shows expression of beta-galactosidase in porcine kidney following in vivo perfusion with AdCMVlacZ virus. The kidney was perfused in situ with a closed-circuit oxygenated system at 37° C. for 2 hours. A kidney biopsy was taken 5 days later and cryosections were stained with X-gal and PAZ. FIG. 4(A) shows intense expression in a large proportion of the glomeruli, while little if any staining was seen in other sections of the kidney. (Magnification 21 times.). FIG. 4(B) shows the staining for beta-galactosidase in mesangial, endothelial, and epithelial cells of a single glomerulus, while cells of the Bowman's capsule are negative. (Magnification 429×)

EXAMPLE 5

Continued experimentation with the variable parameters of perfusion and gene transfer has focused on the conditions of temperature, flow rate of perfusate, and pressure in the perfusion system.

By maintaining low temperature perfusion, about 4° C., for a period of time prior to elevating temperature to around 37° C., it may be possible to facilitate increased adhesion of viral gene therapy vector to the target organ cells. Preliminary results indicate that this protocol of administration can yield high levels of transfer, as indicated by lacZ gene expression as described in the examples above.

Maintaining steady flow rate of perfusate through the organ effects the time of availability/ contact and local effective concentration of viral vectors in the target organ. Preliminary experiments have found that, at about 40 to 60 ml/min flow rate, effective gene transfer via gene therapy viral vectors is achieved. Other flow rates may be more appropriate depending on the characteristics of the target organ and the viral vector being used.

The fluid pressure of the perfusate in the system can effect the efficiency of adhesion of viral vector to the target organ, as well as create stress on the target organ tissue such the intercellular junctions are made more permeable to the invasion of viral vector gene therapy constructs. The pressure in the system must be such that permanent damage to the target organ is avoided, however, pressure may be varied such that there are periods of low pressure. Preliminary experiments have found that in kidney, pressure from about 65 to 200 mm Hg can be maintained, and effective gene therapy transfer via viral vectors can be accomplished.

Materials and methods
DNA Construction and Analysis:

A 5270 bp plasmid containing the full length human α5(IV) collagen cDNA plus an SV40 polyA signal in a pBluescirptSK-vector (Stratagene) was constructed from several cDNA clones and PCR products in many steps. The SV40 polyA sequence was included in the early cloning steps, but not in the final expression constructs. First, a pBluescript plasmid containing the SV40 polyA signal was created. The SV40 polyA signal was amplified by PCR from a pSG5 vector (Stratagene) using a linker sequence in forward primer to create EcoRI, MunI and BglII sites to the 5' end and a XhoI site to the 3' end of the PCR fragment. The fragment was subsequently inserted into the pBluescript vector using the EcoRi and XhoI sites.

A subclone A5-3'XX containing the 3' end of the x5(IV) cDNA linked to SV40 polyA sequence was created by inserting EcoRI(2934)-ApaI(3969) fragment from PL-31 cDNA clone and a ApaI(3969)-EcoRI(5270) fragment from MD-6 cDNA clones (Hostikka S L, Eddy R L. Byers M G. Höyhtyä M. Shows T B. Tryggvason K Identification of a distinct type IV collagen α chain with restricted kidney distribution and assignment of its gene to the locus of X chromosome-linked Alport syndrome. Proc Natl. Acad Sci USA 1990;87:1606–1610) into a pBluescript vector cut with EcoRI. The resulting EcoRI(2934–5270) fragment was ligated into the SV40 polyA signal containing plasmid digested with MunI and EcoRI. The subclones in which the EcoRI(5270) was mutated due to ligation to the MunI site were selected and cut subsequently by XbaI and EcoRI. The XbaI(2404)-EcoRI(2934) fragment from the HT14 cDNA clone (Zhou J. Hertz J M, Leinonen A, Tryggvason K. Complete amino acid sequence of the human α5(IV) collagen chain and identification of a single base mutation in exon 23 converting glysine 521 in the collagenous domain to cystein in an Alport syndrome patient. J Biol Chem. 1992;267:12475–12481) was inserted to create a plasmid A5–3'XX containing the 3' half of the cDNA. The numbering starts from base 1 at the 5' of the cDNA (Zhou et al. 1992).

A plasmid A5-5'NX containing the 5' half of the cDNA was created by ligating the following three DNA fragments into the pBluescript vector linearized with NotI and XbaI: a) Notd-AvaI(420) from a JZ-4 cDNA clone (Zhou et al. 1992) subcloned to the pBluescript vector; b) AvaI(420)-AccI(768) PCR fragment amplified from the HT14 cDNA template using a forward primer extending to the AvaI(420) site (HT14 starts at 444);c) AccI(768)-XbaI(2404) from the HT14 cDNA clone.

To generate a plasmid construct pA5-UFL containing the full-length coding sequence for the α5(IV) chain, the XbaI (2404)-XhoI fragment was recovered from the A5-3'XX plasmid and ligated into the A5-5',NX plasmid cut with XbaI-XhoI.

To facilitate recombinant protein purification and distinction from the endogenous α5(IV) collagen the full-length α5(IV) cDNA was modified to contain a nucleotide sequence encoding the FLAG epitope, an octapeptide with the amino acid sequence DYKDDDDK. The FLAG sequence was added to the sequence encoding the fifth interruption in the collagenous domain by oligonucleotide-directed mutagenesis. A forward primer homologous to 1033–1052 in the cDNA sequence and a mutagenic primer 5'-TTCTCCTATAGTTATCTTGTCATCGT-CGTCCTTGTAGTCTCTAGGAATTAC AAGTCCA-3' containing the FLAG encoding sequence was used to amplify a 254 bp megaprimer which was used after purification as a primer in a second PCR reaction with a reverse primer homologous to nucleotides 1702–1721. The HT14 cDNA clone was used as a template. The 700 bp PCR product was digested with MscI(1120) and HincII(1683) and inserted using the same enzymes into the A5-5'NX which was earlier modified by deleting the HincII site from the polylinker. The sequence of the PCR fragment and the cloning sites of the resulting plasmid were verified by sequencing and the NotI-Xba(2404) insert was ligated into the A5-3'XX plasmid to generate the pA5-UFLAG plasmid. The inserts of the pA5-Uwt and pA5-UFLAG plasmids were sequenced to check the presence of possible mutations and used in an in vitro translation assay (TNT coupled reticulocyte lysate system, Promega) to ensure the translation of a full-length polypeptide chains (185 kDa).

To increase the expression level of the recombinant protein, the translation initiation signal of α5(IV) cDNA was replaced by a modified Kozak translation initiation sequence (Kozak M. Determinants of translational fidelity and efficiency in vertebrate mRNAs. Biochimie 1994;76:815–821). A forward primer 5'-AAGGAAAAAAGCGGCCGCAAGCTT-GCCGCCACCATGGAACTGCGTGGAGT-CAGCCT-3' homologous to α5(IV) cDNA at position 203–225, plus containing a modified translation initiation signal and restriction sites for NotI and HindIll, and a reverse primer homologous to 417–440, was used to amplify a 270 bp PCR fragment using HT14 cDNA clone as a template. The PCR product was digested with NotI-AvaI(420) and subcloned together with the AvaI(420)-XbaI(2404) insert from the pA5-Uwt and pA5-UFLAG into the A5-3'XX plasmid linearized with NotI-XbaI to generate the plasmid pA5-Uwt-205 and pA5-UFLAG-205 respectively.

To produce recombinant transfer vectors the NotI—BgIII inserts of pA5-UFL-205 and pA5-UFLAG-205 were ligated into a defosforylated pAdBM5pAG vector (Quantum Biotechnologies) digested with BamHI. The unligated ends were treated by Klenow and phenol extracted and subsequently blunt end ligated to form circular transfer plasmids called pAdBM5pAG+Uwt and pAdBM5pAG+UFLAG.

Construction and Purification of Recombined Adenoviruses

Adenoviral recombinants (Ad-A5 FLAG and Ad-A5 wt) containing the 5.2 kb cDNA coding for α5(IV) type IV collagen chain with and without a FLAG tag were constructed using an Adeno-Quest Adenovirus expression system (Quantum Biotechnologies). Briefly, E1/E3 delete replication defective serotype 5 human adenovirus (AdCMVlacZΔE1/ΔE3) DNA and the ClaI cut recombinant transfer vectors pAdBM5pAG+Uwt and pAdBM5pAG+UFLAG were co-transfected into 293A cells. The recombinant virus plaques were purified by consecutive plaque assays and the viral clones expressing the α5(IV) chain were characterized by PCR and Western blotting using anti FLAG-M2 and anti α5(IV) chain H53 antibodies. The adenoviral stocks were purified twice by ultracentrifugation through a $CsCl_2$ gradient, followed by desalting on Econopac columns (Bio-Rad). The titers of the virus stocks were assessed by plaque assays. Human adenovirus AdCNfVlacZ, used as a control, was amplified and purified as above. The viral preparations were tested for replication competence by extended cultivation on HeLa cells.

Infection of Human Cells in Vitro

HT1080 or 293A cells were cultured in DMEM (GIBCO-BRL) containing 10% FCS and penicillin/streptomycin until 80% confluency. The cells were infected with the adenovirus Ad-A5FLAG and Ad-A5 WT at MOI 1000 in a serum free medium for 3 hours. The virus containing medium was rinsed off and the cells were fed by serum free medium containing 100 μg/ml ascorbate. 50 μg/ml of ascorbate was added daily to ensure posttranslational modifications of collagenous proteins.

Protein analysis, Purification, Antibodies and Immunoblotting

Three days after infection, the cells were collected and lysed in the SDS sample buffer. The medium was collected and centrifuged at 8000 rpm for 10 minutes, and used in immunoprecipitation or concentrated by precipitation with 70% ethanol in −20° C. for one hour. After centrifugation at 8000 rpm for 1 hour in +4° C., the pellets containing the precipitated proteins were suspended into SDS-sample buffer and used in SDS-PAGE.

FLAG tagged recombinant protein was purified by monoclonal anti-FLAG M2 affinity chromatography (Eastman Kodak Scientific Imaging Systems, New Haven, Conn.), as described in the manufacturer's instructions. The protein was eluted by boiling in SDS sample buffer containing mercaptoetanol, separated in 6% SDS-PAGE and analyzed on immunoblots using monoclonal antibodies H11, H22, H31, H44, H53 and H63 against the type IV collagen α1 to α6 chains, respectively (Sado Y, Kagawa M, Kishiro Y, Sugihara K, Naito I, Seyer J M, Sugimoto M, Oohashi T, Ninomiya Y, Establishment by the rat lymph node method of epitope-defined monoclonal antibodies recognizing the six different a chains of human type IV collagen. Histochem Cell Biol. 1995;104:267–275, Kagawa M. Kishiro Y, Naito I, Nemoto T, Nakanishi H, Ninomiya Y, Sado Y. Epitope-defined monoclonal antibodies against type IV collagen for diagnosis of Alport's syndrome. Nephrol Dial Transplant 1997;12:1238–1241).

In Vivo Administration of Adenovirus Into the Pig Kidney by Organ Perfusion

In vivo perfusion was carried out essentially as previously reported (Heikkilä P. Parpala T. Lukkarinen O. Weber M. Tryggvason K. Adenovirus-mediated gene transfer into kidney glomeruli using an ex vivo and in vivo kidney perfusion system—first steps towards gene therapy of Alport syndrome. Gene Therapy 1996;3:21–27). Briefly, young farm pigs were anesthetized, and the left kidney was exposed through laparotomy. The renal artery and vein were clamped and cannulated. The cannules were tied to silicon tubing connected to the perfusion device. The perfusion was performed in a closed-circuit mode where the oxygenated and heated (37° C.) perfusate was recirculated continuously through the kidney. The perfusate solution (about 250 ml) contained previously separated and serotyped porcine red blood cells (17% hematocrit value), 10 000 U heparin (Lövens), 100 mg Cefuroxim (Glaxo) in Krebs-ringer solution. Prior to connection of the renal arterial inlet to the perfusion device, 18 ml of 0.9% NaCl solution containing 180 mg lidocain and 5000 U heparin were infused into the renal artery, followed by infusion of the adenovirus solution in 9 to 14 ml. The kidney was exposed to 15 min warm ischemia before connecting the perfusion with the oxygenated perfusate. Ureterostomy was made to collect and recirculate the urine formed during the perfusion. The perfusions were carried out for 120 minutes with a perfusion flow of 53 ml/min and arterial pressure 150–200 mmHg. After that, the cannules were removed and the puncturing sites and the uterostomy were sutured. The wound was closed and 100 mg of Solu-Cortef® (Upjohn) and 1000 U of Heparin were given post-operatively. Four days later, the animals were sacrificed and the kidneys were analyzed by histochemical and immunohistochemical methods.

In Situ Hybridization

For in situ hybridization tissues from pig kidney were fixed in the fresh 4% paraformaldehyde, dehydrated in ethanol, embedded in paraffin and sectioned. Following postfixation in the 4% paraformaldehyde, the sections were incubated in PBS containing 0.1% active diethyl pyrocarbonate (Sigma), equilibrated in 5 xSSC and prehybridized for 2 h at 55° C. Hybridization was carried out overnight at 550° C. with an 172 bp probe encoding the NCI domain of the α5(IV) chain. Antisense and sense riboprobes were generated using digoxigenin (DIG)-11-UTP by in vitro transcription with T7 and T3 RNA polymerase (Boehringer Mannheim). After washing in 50% formamide and standard sodium citrate, the sections were incubated with an alkaline phosphatase coupled anti-DIG antibody and were colored by the nitro blue tetrazolium and 5-bromo-4-chloro-3-indolyl phosphate (NBTIBCIP) solutions Boehringer Mannheim).

Immunohistochemical and Histochemical Analysis of Kidney Tissues

Kidney tissues were studied for galactosidase expression h, X-2al- staining (Heikkilä P. Parpala T. Lukkarinen 0. Weber M. Tryggvason K. Adenovirus-mediated gene transfer into kidney glomeruli using an ex vivo and in vivo kidney perfusion system—first steps towards gene therapy of Alport syndrome. Gene Therapy 1996;3:21–27). In immunohistological studies the anti FLAG-M2 and anti α5(IV) chain antibodies H52 were used. Cryosections were fixed using aceton, treated with 50 mM HCl, 50 mM KCl and blocked using 5% normal pig serum. M2 antibodies were diluted to 1:100 and the H-series antibodies 1:70 and the staining was carried out using an FITC-labeled secondary antibody (DAKO).

Results

Adenovirus Vectors for Expression of the Type IV Collagen α5 Chain

For expression of the type IV collagen α5 chain two constructs were made (FIG. 2.). The first adenovirus, Ad-A5 wt contained the full-length human coding sequence for the α5(IV) chain (Zhou J. Hertz J M, Leinonen A, Tryggvason K. Complete amino acid sequence of the human α5(IV) collagen chain and identification of a single base mutation in exon 23 converting glysine 521 in the collagenous domain to cystein in an Alport syndrome patient. J Biol Chem. 1992;267:12475–12481), and the second contained the same cDNA with an additional FLAG sequence-tag. The FLAG tag was used to enable easy purification of the recombinant a chain, as well as to distinguish it from the endogenous one in tissues following in vivo gene transfer in pigs. The eight-residue FLAG tag sequence was placed in a 10-residue noncollagenous sequence in the fifth interruption in the collagenous domain of the α5 chain. This interruption coincides with interruptions in all other α(IV) chains and it is not known to have any special role, other than to provide a kink in the molecule. The interruption does e.g. not contain cell binding sites or cross-linking amino acids and, furthermore, none of the over 300 different missense mutations now identified in the α(IV) chain in Alport syndrome is located in this interruption. Consequently, it was considered likely that the FLAG sequence would not interfere with assembly of this chain into a triple-helical molecule. In addition to this modification, the translation initiation signal in both constructs was modified to contain the optimal context for initiation of translation according to Kozak (Kozak M. Determinants of translational fidelity and efficiency in vertebrate mRNAs. Biochimie 1994;76:815–821). The two types of adenoviruses were made by homologous recombination, and the recombinant viral plaques were purified by plaque assays. The cDNA sequence encoding human α5(IV) cDNA was shown to be correct as determined by DNA sequencing.

Characterization of Recombinant Type IV Collagen α5 Chains Expressed with Adenovirus Vectors in Human Cells Expression of the α(IV) chain was first detected by in vitro translation of a 180 kDa polypeptide. Adenoviral expression of the α5(IV) in infected 293A cells was detected by immunoblotting of the protein from cell lysates and media. The recombinant α5 chain was detected as a band of about 200 kDa (FIG. 7), using either an anti-FLAG antibody or a monoclonal anti-α5(IV) antibody H53 made against a peptide sequence in the third interruption in the collagenous domain (Kagawa M, Kishiro Y, Naito I, Nemoto T. Nakanishi H, Ninomiya Y, Sado Y. Epitope-defined monoclonal antibodies against type IV collagen for diagnosis of Alport's syndrome. Nephrol Dial Transplant 1997;12:1238–1241). The increase in size in vivo versus in vitro can be explained by glycosylation and other cellular post-translational modifications. The H53 antibody recognized polypeptide chains produced with both constructs, while the anti-FLAG antibody recognized only the a chain with a FLAG marker. Both antibodies recognized from the medium additional two bands of about 100 kDa and 130 kDa which probably represent degradation products.

Figure 7:
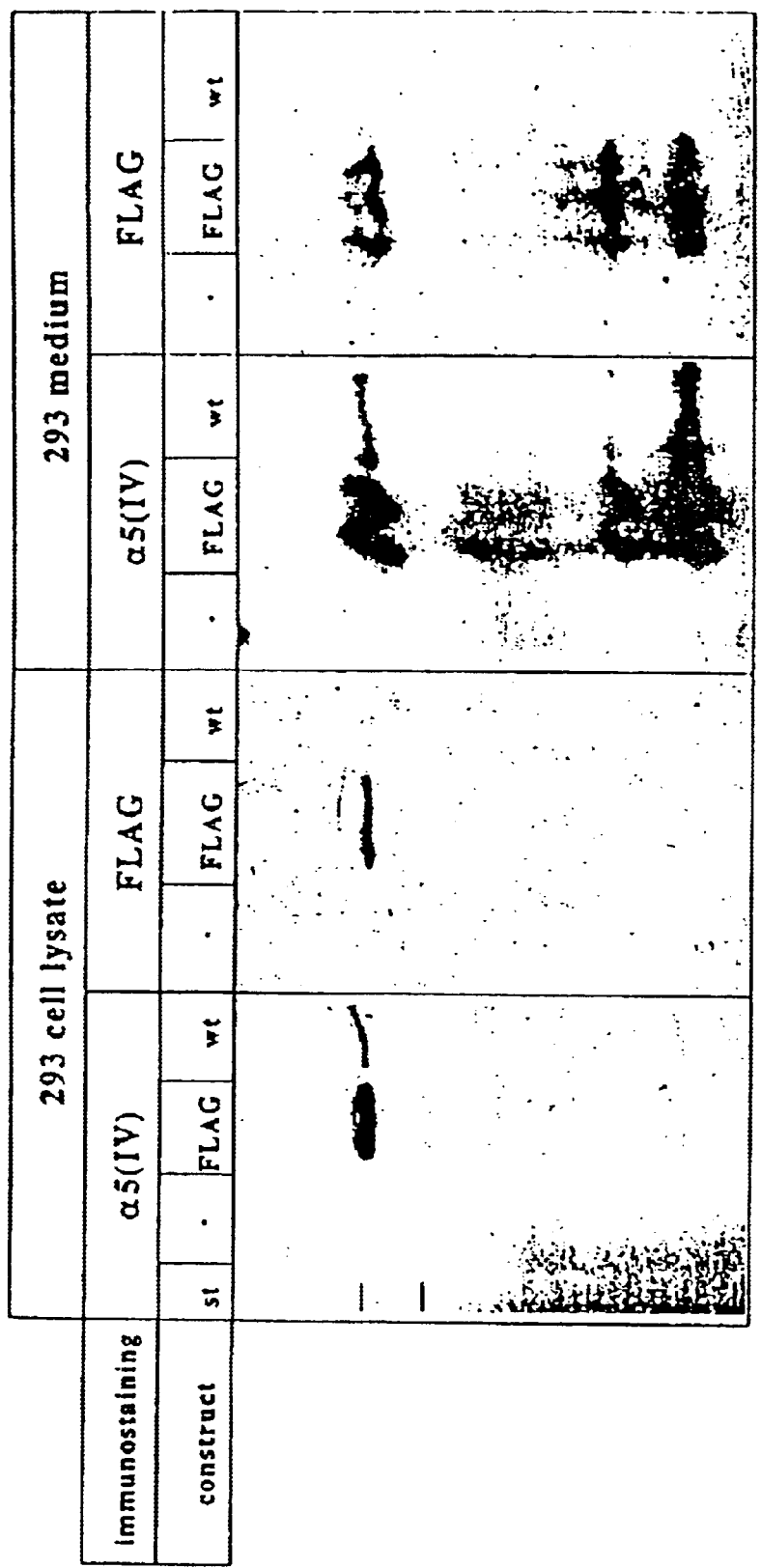
FIG. 7 illustrates the characterization of recombinant α5(IV) chains produced with adenovirus in 293 human embryonic kidney cells.
Figure 8:
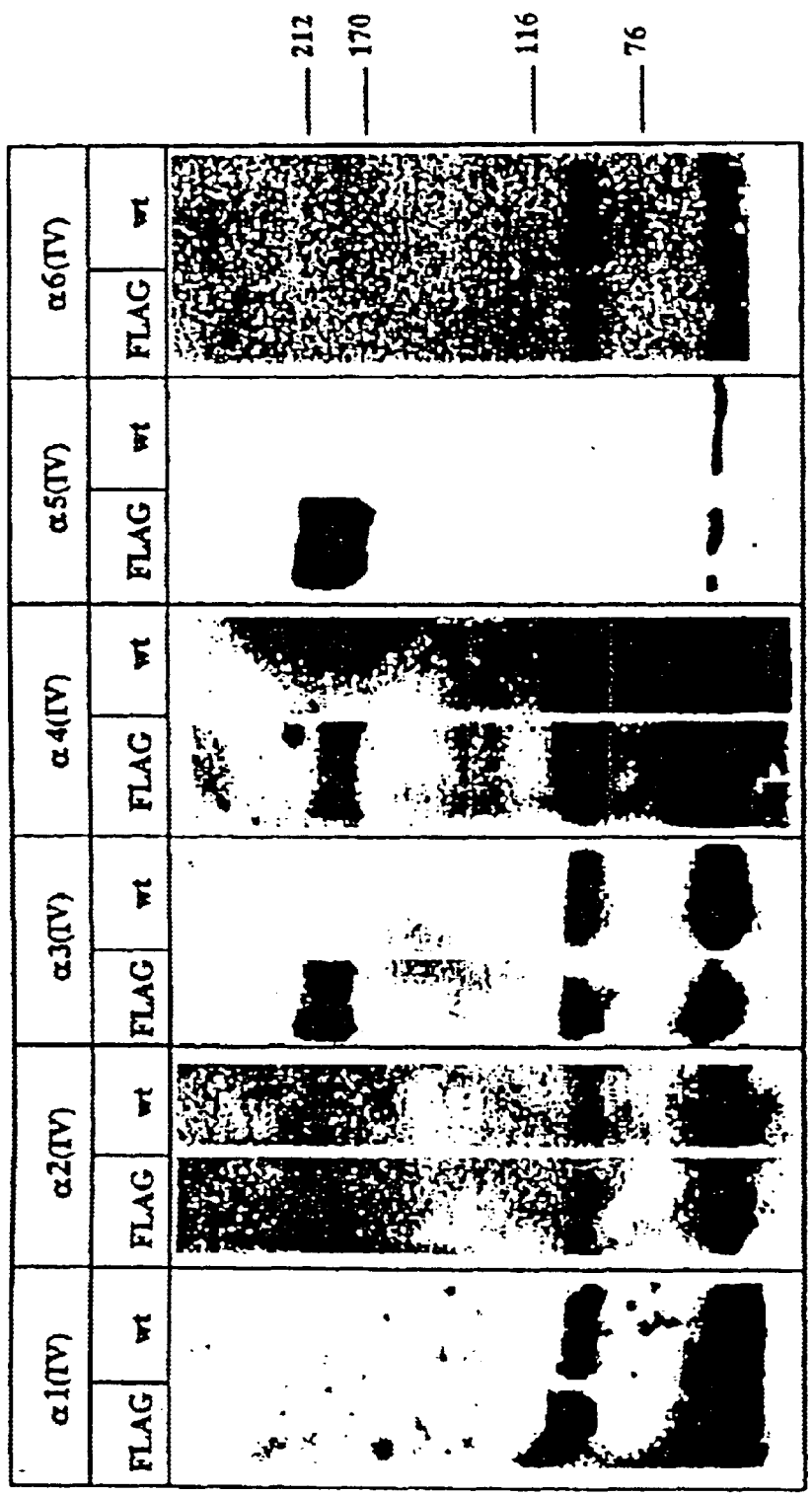
FIG. 8 depicts the chain composition of type IV collagen molecules containing the recombinant α5(IV) chain produced in HT1080 cells with adenovirus.

Chain Composition of Secreted Type IV Collagen Molecules Containing the Recombinant α5(IV) Chain In order to study with which a chains the recombinant α5 chain can assemble in a triple-helical collagen molecule, the chain was expressed in human HT1080 cells that normally express the α1(IV)–α5(IV) collagen chains, but not α6(IV). The α1(IV), α2(IV) and α5(IV) chains normally synthesized and secreted by these cells were easily detectable in western blots from the medium, while the α3(IV) and α4(IV) chains were synthesized in so small amounts that they were only detectable in the cell lysate. Following infection of the cells with the adenovirus, construct containing α(IV) cDNA with the FLAG sequence tag the α5(IV) chain was detectable in cell lysate and medium in western blot using anti-FLAG antibodies. The recombinant α5-FLAG chain present in the medium was mainly as a single chain without assembling with the other endogenous α(IV) chain, but some of it was assembled with other (x(IV) chains. To study the chain composition of trimers containing the α5-FLAG chain, medium protein was immunoprecipitated with the anti-FLAG antibody. The immunoprecipitate was found to contain α3(IV) and α4(IV) chains, in addition to the α5-FLAG chain as shown by western blotting with chain specific monoclonal antibodies (FIG. 7). Also a minor band was visible by staining with an antibody against the α2(IV) chain. The α1(IV) chain was not contained at all in immunoprecipitates obtained with the anti-FLAG antibody. Furthermore, the α6 chain was never seen, which is simply explained by the fact that the α6(IV) chain is normally not expressed by this cell line. The immunoprecipitated medium from cells expressing the wt construct, used as a control in the immunoprecipitations, was negative for all a chain staining (FIG. 7).

Analysis of Expression of a Recombinant α5 (IV) Chain mRNA and Protein in Tile Porcine Kidneys Followed by Organ Perfusion in Vivo To study if the recombinant α5(IV) type IV collagen can be expressed in vivo in kidney glomeruli, we used the perfusion method for adenoviral gene transfer in pigs (Heikkilä P, Parpala T, Lukkarinen O, Weber M, Tryggvason K, Adenovirus-mediated gene transfer into kidney glomeruli using an ex vivo and in vivo kidney perfusion system-first steps towards gene therapy of Alport syndrome. Gene Therapy 1996;3:21–27). Porcine kidney was isolated from the systemic blood circulation with clamps on the renal artery and vein, and perfused using a separate oxygenated system as previously described (Heikkilä et al., 1996). Samples of $5\times10^{11}$ pfu of adenovirus Ad-A5FLAG and $5\times10^{11}$ pfu Ad5 CMVlacZ adenovirus. Ad5CMVlacZ were used to evaluate gene transfer efficiency in each experiment. Gene transfer efficiency as measured by X-Gal staining of tissue slides, varied between 10–50% positive glomeruli of all glomeruli in each kidney, significant variation between different areas in kidney cortex being observed. As reported before, other structures in kidney than glomeruli were negative, only glomerular cells showed positive staining.

Figure 9B:
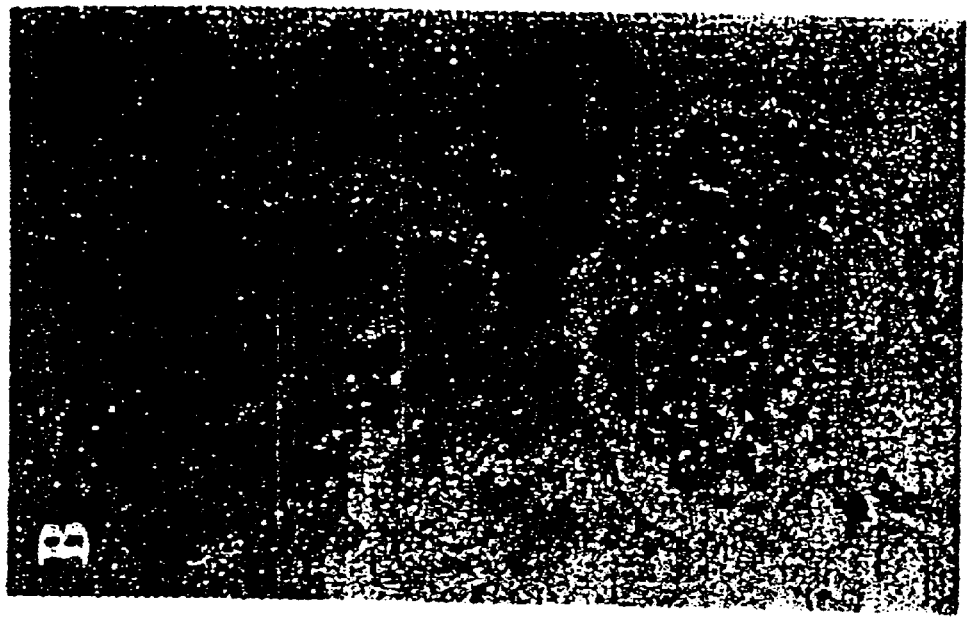
FIG. 9B depicts a control kidney having no signals with the α5(IV) chain probe.
Figure 9A:
FIG. 9A shows in situ hybridization of the α5(IV) chain mRNA in kidney tissue following adenovirus-mediated gene transfer in vivo revealing expression in a large proportion of the glomeruli.
Figure 10A:
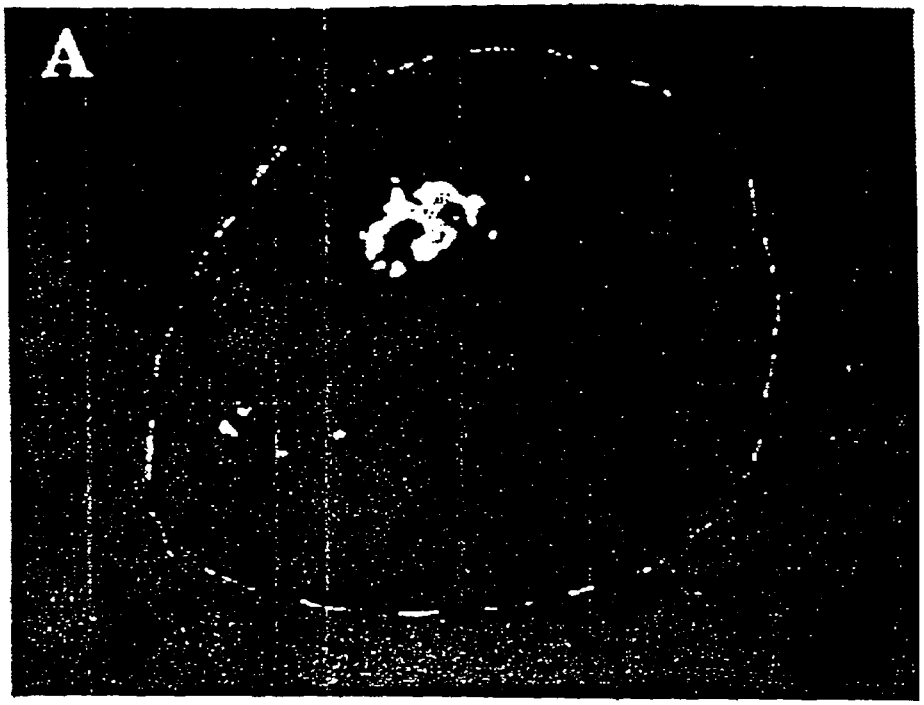
FIGS. 10A and 10B shows inmunolocalization of recombinant α5(IV) chain in pig kidney following adenovirus-mediated gene transfer in vivo.
Figure 10B:
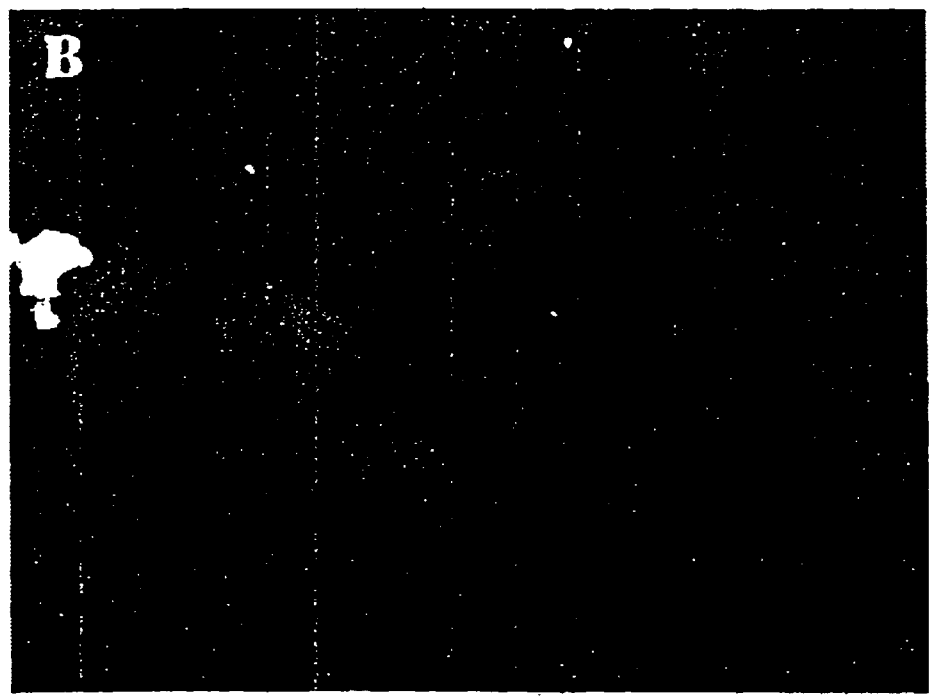

To analyze expression of the recombinant α5(IV) chain in the kidney, mRNA for the α5 chain was visualized by in situ hybridization (FIGS. 9A and 9B) using a 172 bp probe from cDNA encoding the NC1 domain of the human α5(IV) collagen chain. The staining pattern in the kidney was similar to that obtained with X-gal staining. Thus, the Ad-A5 FLAG virus infect the same cell types as the β-galactosidase expressing virus. Endogenous α5(IV) chain in porcine tissues was not detected by this method (FIG. 9B). The amount of the endogenous α5(IV) chain mRNA is possibly very low, or porcine mRNA which has not been sequenced, is not completely homologous with human one.

The recombinant α5(IV) chain was also detected by immunofluoresence using FLAG antibodies. Positive staining was detected only in glomeruli. In glomeruli some highly positive cells were obtained. More importantly some positive deposits of linear GBM staining were obtained implying that recombinant α5(IV) chain can be incorporated to the GBM. The control kidney showed no positive staining.

The methods of the instant invention allow for a prolonged period of administration of pharmaceuticals to a target by way of re-circulating a pharmaceutical containing solution through the target such that a perfusion effect occurs. The methods of the instant invention allow for prolonged administration because of the unique use of the perfusion method and the oxygenation of the pharmaceutical containing solution. In one embodiment, the perfusion apparatus and target forms a closed system whereby the pharmaceuticals are administered at a starting concentration and not adjusted during the time course of treatment. In another embodiment, the pharmaceutical concentration is periodically adjusted so as to maintain or otherwise alter the concentration of pharmaceutical in the solution, or additional pharmaceuticals are added. In a preferred embodiment, the solution does not require replenishment during the course of treatment. In another embodiment, the solution volume can be replenished as leakage or other forms of loss occur during the course of treatment. (The term "solution," as used herein refers to the medium in which the pharmaceutical is suspended, dissolved or otherwise maintained for delivery to the target, aka. the perfusate, and includes blood, serum, plasma, saline, and/or buffered solutions.) In a preferred embodiment, 350 ml of perfusate contains red blood cells (around 17% of hemocrit value), and can include about 25,000 IU heparin, about 20,000 IU penicillin and about 20,000 μg streptomycin in Krebs-Ringer solution in addition to the pharmaceutical.

While the invention has been described with respect to certain specific embodiments, it will be appreciated that many modifications and changes may be made by those skilled in the art without departing from the spirit of the invention. It is intended, therefore, by the appended claims to cover all such modification and changes as fall within the true spirit and scope of the invention.

We claim:

1. An improved method for gene therapy of kidney disorders, wherein the gene therapy comprises contacting the kidney of a patient with a kidney disorder with an amount effective for treatment of the disorder of a viral vector gene therapy pharmaceutical for treatment of the disorder, wherein the improvement comprises contacting the patient's kidney with the viral vector gene therapy pharmaceutical in a re-circulating, oxygenated perfusate solution, and where the perfusate solution is held at about 37° C., such that there is effective delivery of the viral vector gene therapy pharmaceutical.

2. The method of claim 1 wherein the target is in vivo and in situ.

3. The method of claim 1 wherein the target is ex vivo.

4. The method of claim 1 wherein the mammalian target tissue is selected from kidney, liver, mammary glands, spleen, and lung.

5. A method for the extended delivery of a pharmaceutical to mammalian kidney tissue comprising contacting the mammalian kidney tissue with the pharmaceutical in a re-circulating, oxygenated perfusate, where the perfusate solution is held at about 37° C., such that there is effective delivery of the viral vector gene therapy pharmaceutical.

6. The method of claim 5 wherein the target is in vivo and in situ.

7. The method of claim 5 wherein the target is ex vivo.

8. A method for the effective delivery of a viral vector gene therapy pharmaceutical to a mammalian kidney tissue comprising contacting the mammalian kidney tissue with the viral vector gene therapy pharmaceutical in a re-circulating, oxygenated perfusate solution, where the solution is held at about 37° C., such that there is effective delivery of the viral vector gene therapy pharmaceutical.

9. The method of claim 8 wherein the target is in vivo and in situ.

10. The method of claim 8 wherein the target is ex vivo.

11. An improved method for gene therapy of kidney disorders, wherein the gene therapy comprises contacting the lung of a patient with a kidney disorder with an amount effective for treatment of the disorder of a gene therapy pharmaceuticals for treatment of the disorder, wherein the improvement comprises contacting the patient's kidney with the gene therapy pharmaceutical in a re-circulating, oxygenated perfusate solution, and where the perfusate solution is held at about 37° C., such that there is effective delivery of the viral vector gene therapy pharmaceutical.

12. The method of claim 11, wherein the kidney disorder is Alport syndrome.

* * * * *